US009784685B2

(12) United States Patent
Atzler et al.

(10) Patent No.: US 9,784,685 B2
(45) Date of Patent: Oct. 10, 2017

(54) LIQUID AND PLATE SENSORS FOR MICROPLATE INJECTOR SYSTEM

(71) Applicant: Molecular Devices, LLC, Sunnyvale, CA (US)

(72) Inventors: Josef J. Atzler, Hallein (AT); Michael Katzlinger, Eugendorf (AT); Georg Kronberger, Salzburg (AT); Bernhard Schinwald, Munderfing (AT)

(73) Assignee: Molecular Devices, Inc., Sunnyvale, CA (US)

( * ) Notice: Subject to any disclaimer, the term of this patent is extended or adjusted under 35 U.S.C. 154(b) by 9 days.

(21) Appl. No.: 14/566,708

(22) Filed: Dec. 10, 2014

(65) Prior Publication Data

US 2016/0169808 A1    Jun. 16, 2016

(51) Int. Cl.
| | | |
|---|---|---|
| *G01N 35/02* | (2006.01) | |
| *G01N 21/64* | (2006.01) | |
| *G01N 35/10* | (2006.01) | |
| *G01J 3/02* | (2006.01) | |
| *G01N 21/76* | (2006.01) | |
| *G01J 3/00* | (2006.01) | |
| *G01N 21/25* | (2006.01) | |

(52) U.S. Cl.
CPC ............... *G01N 21/76* (2013.01); *G01J 3/02* (2013.01); *G01N 35/028* (2013.01); *G01N 21/253* (2013.01); *G01N 21/763* (2013.01); *G01N 2035/1025* (2013.01)

(58) Field of Classification Search
None
See application file for complete search history.

(56) References Cited

U.S. PATENT DOCUMENTS

| | | | | | |
|---|---|---|---|---|---|
| 5,290,513 | A | * | 3/1994 | Berthold | G01N 21/76 250/328 |
| 5,611,994 | A | * | 3/1997 | Bailey | G01N 21/253 250/361 C |
| 5,682,232 | A | * | 10/1997 | Tajima | G01N 35/028 250/361 C |
| 8,119,066 | B2 | | 2/2012 | Stock et al. | |
| 2004/0189311 | A1 | * | 9/2004 | Glezer | B01L 3/5027 324/444 |
| 2008/0031774 | A1 | * | 2/2008 | Magnant | B01L 3/5085 422/63 |
| 2012/0077282 | A1 | | 3/2012 | Katzlinger et al. | |

(Continued)

*Primary Examiner* — Neil N Turk
(74) *Attorney, Agent, or Firm* — Olive Law Group, PLLC; David P. Gloekler

(57) ABSTRACT

In a sample analyzing apparatus, an injector assembly injects a reagent onto a sample, and luminescent light from the sample is transmitted to a detector. The assembly may be movable toward and away from the sample. The assembly may include one or more needles that communicate with one or more reservoirs supplying reagent or other liquids. The assembly may include a light guide for communicating with the detector. A cartridge may be provided in which the assembly, one or more reservoirs, and one or more pumps are disposed. The cartridge and/or the apparatus may be configured for enabling rinsing or priming to be done outside the apparatus. The cartridge and/or the apparatus may include one or more types of sensors configured for detecting, for example, the presence of liquid or bubbles in one or more locations of the apparatus and/or the cartridge.

29 Claims, 24 Drawing Sheets

(56) References Cited

U.S. PATENT DOCUMENTS

2013/0299686 A1* 11/2013 Freeman .............. G01N 21/253
250/252.1
2014/0191138 A1 7/2014 Atzler et al.

* cited by examiner

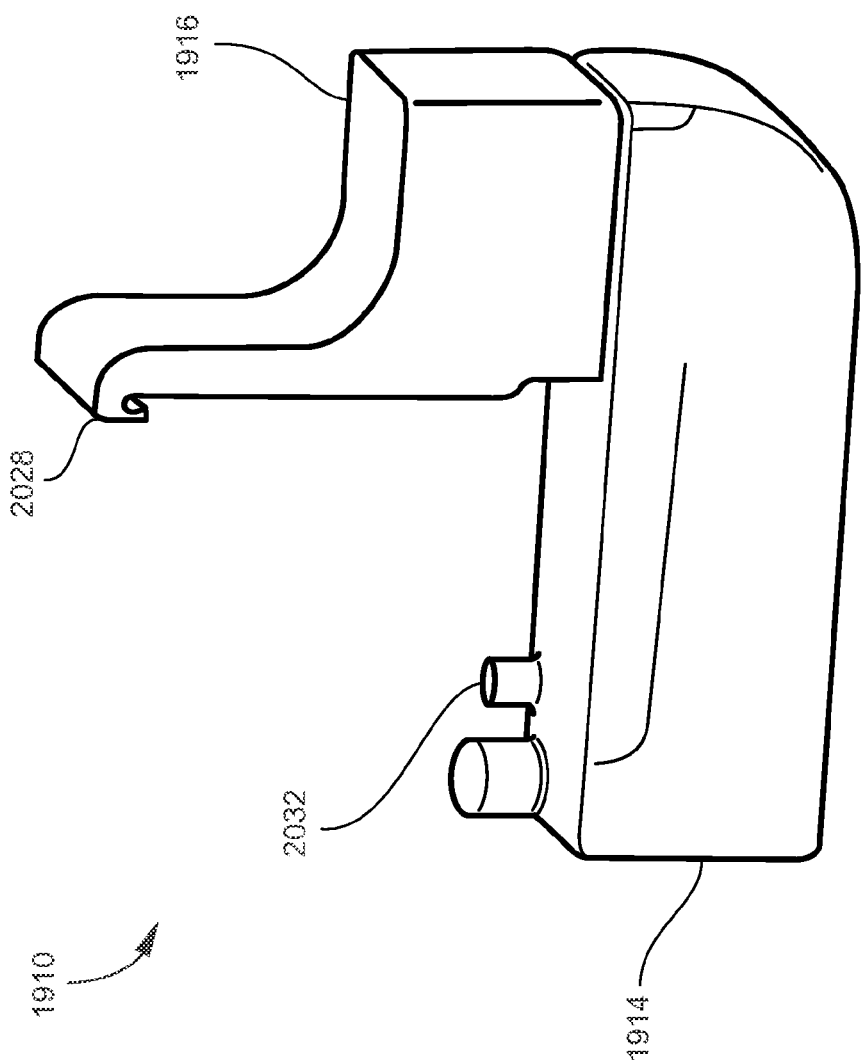

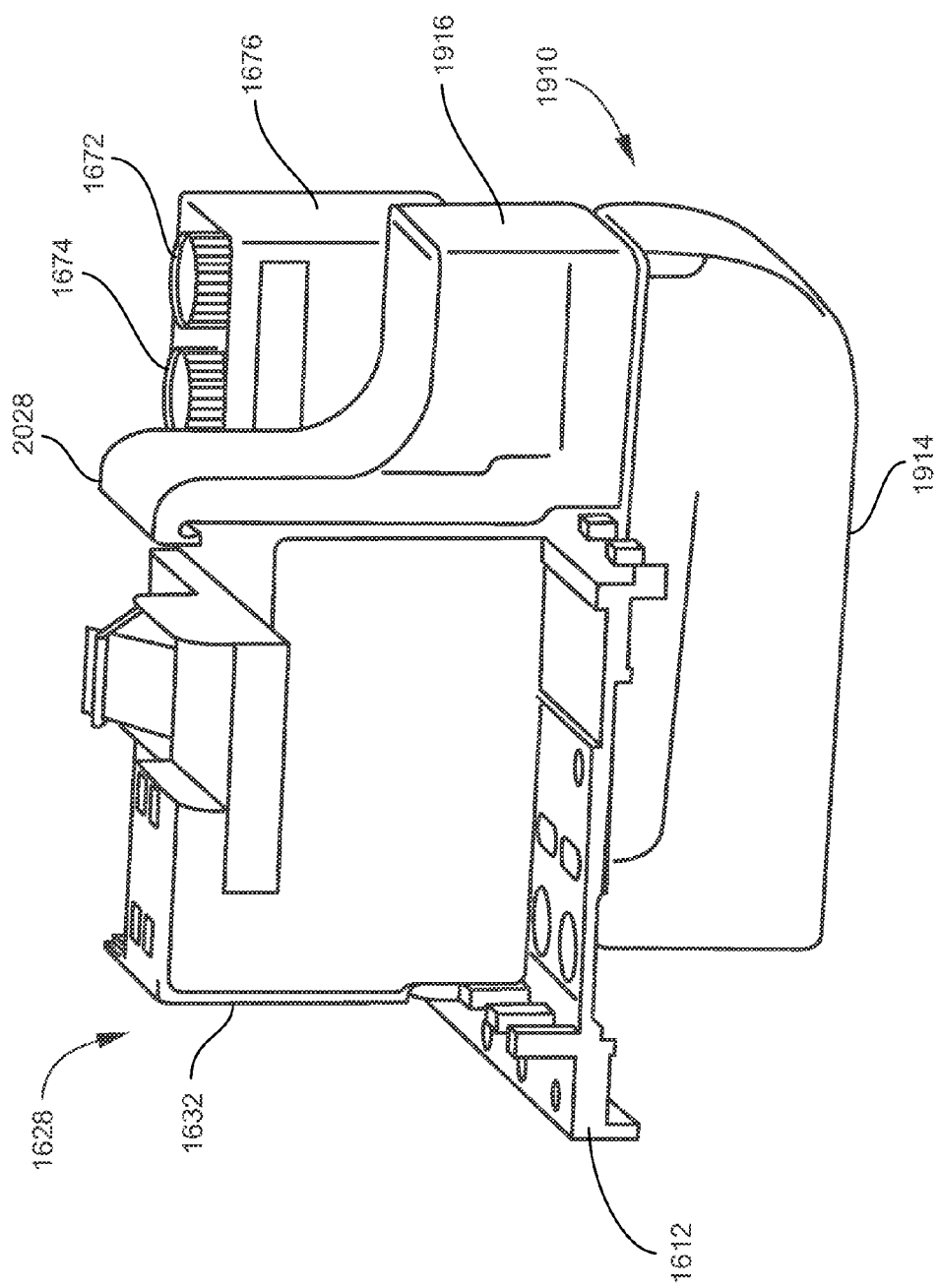

LIQUID AND PLATE SENSORS FOR MICROPLATE INJECTOR SYSTEM

TECHNICAL FIELD

This present invention generally relates to analytical instruments, including multimode analytical instruments and cartridges utilized with such instruments, and methods related to such instruments and cartridges. In particular, the invention relates to measuring luminescent emissions from samples utilizing such instruments, cartridges and methods, and to addressing problems associated with the use of reagents and other liquids in conjunction with luminescence measurement.

BACKGROUND

Various analytical instruments have been developed for making optics-based measurements (e.g., fluorescence, luminescence, and absorbance) as part of assays useful in the life science industry. Many analytical instruments are designed to carry out only one or a few dedicated types of measurements. On the other hand, multimode analytical instruments, also referred to as multimode readers, are designed to perform multiple analytical assays in a single instrument. Multimode analytical instruments may be designed to be re-configurable to enable a user to select different types of measurements to be performed. Some multimode analytical instruments utilize application-specific cartridges to enable re-configuration. Examples of multimode analytical instruments are described in U.S. Patent Application Nos. 2005/0012929; 2005/0105080; and 2003/0048447, for example. Additional examples include U.S. Pat. No. 8,119,066, and U.S. Patent Application Pub. No. 2012/0077282.

In the case of performing flash luminescence, a reagent must be injected onto the sample to induce the luminescent response. In the case of multimode readers that utilize cartridges, there is a need for integrating the reagent injection function and the luminescence reading function into a single cartridge. Moreover, because luminescence experiments require a fluidic system to dispense reagent liquid, such a system must be periodically rinsed and primed, and possibly cleaned or decontaminated. Hence, luminescence experiments may entail a variety of different types of liquid flows, which may lead to undesired contamination of optics components of the sample analyzing apparatus and other problems. As examples, contamination may result from electrostatically accelerated droplets, the generation of uncontrolled droplet sizes, the unwanted dispensing or spilling of liquid onto sensitive optics components, and the development of leaks in the fluidic system. Therefore, there is also a need for sample analyzing apparatuses, including those utilizing luminescence cartridges, which address such problems.

SUMMARY

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to one embodiment, a sample analyzing apparatus includes: an apparatus housing; a sample carrier disposed in the apparatus housing and configured for supporting a sample; a reagent reservoir; a pump communicating with the reagent reservoir; an injector assembly disposed in the apparatus housing and comprising an injector housing and an injector needle extending through the injector housing and configured for communicating with the reagent reservoir via the pump; and a luminescence detector positioned in the apparatus housing to receive optical signals from the sample.

According to another embodiment, the sample analyzing apparatus includes a luminescence cartridge removably mounted at the sample analyzing apparatus, the luminescence cartridge comprising a cartridge housing comprising a cartridge housing opening, and a driver disposed in the cartridge housing, wherein the reservoir support and the pump are disposed in the cartridge housing, and the injector assembly is at least partially disposed in the cartridge housing and is movable by the driver through the cartridge housing opening and alternately toward and away from the sample carrier.

According to another embodiment, a luminescence cartridge for use in a sample analyzing apparatus includes: a cartridge housing comprising a cartridge housing opening; a reservoir support disposed in the cartridge housing and configured for supporting a reagent reservoir; a pump communicating with the reagent reservoir; a driver disposed in the cartridge housing; an injector/reader assembly at least partially disposed in the cartridge housing and comprising an injector/reader housing, an injector needle extending through the injector/reader housing and configured for communicating with a reagent reservoir supported by the reservoir support via the pump, and a light guide extending through the injector/reader housing and configured for communicating with a luminescence detector, wherein the injector/reader assembly is movable by the driver through the cartridge housing opening and alternately toward and away from the cartridge housing; and an electrical connector mounted at the cartridge housing and in signal communication with the driver and the pump, the electrical connector configured for removable coupling to the sample analyzing apparatus to receive power from and transmit signals to or from the sample analyzing apparatus.

According to another embodiment, a sample analyzing apparatus includes: a luminescence cartridge according to any of the embodiments disclosed herein; an apparatus housing; a sample carrier disposed in the apparatus housing; and a cartridge support configured for receiving the luminescence cartridge such that the luminescence cartridge is removably mounted thereto, the cartridge support movable between an inside cartridge support position at which the cartridge support is positioned entirely in the apparatus housing and an outside cartridge support position at which the cartridge support is positioned at least partially outside the apparatus housing, wherein: the injector/reader assembly is movable by the driver alternately toward and away from the sample carrier; and at least one of the sample carrier and the cartridge support is movable to align the injector/reader assembly with a sample contained on the sample carrier.

According to another embodiment, a method for analyzing a sample includes: positioning an injector assembly in alignment with and at a desired distance from a sample in a sample analyzing apparatus, the injector assembly comprising an injector housing and an injector needle extending through the injector housing; injecting a reagent from the injector needle to the sample by operating the pump to establish a flow of the reagent from a reagent reservoir to the injector needle; and detecting luminescent light emitted from the sample at a luminescence detector.

According to another embodiment, the sample analyzing apparatus comprises a cartridge support, and the method further includes: loading a luminescence cartridge on the cartridge support, wherein the luminescence cartridge comprises a cartridge housing comprising a cartridge housing opening, the pump and the reagent reservoir are disposed in the cartridge housing, and the injector assembly is at least partially disposed in the cartridge housing and extends through the cartridge housing opening; and before aligning the injector assembly with the sample, moving the luminescence cartridge into an apparatus housing of the apparatus by operating the cartridge support.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

FIG. 14 is a perspective view of an example of the external rinsing/priming station according to some embodiments.

FIG. 15 is a perspective view of the external rinsing/priming station illustrated in FIG. 14 as mounted to a cartridge support and/or a luminescence cartridge.

DETAILED DESCRIPTION

According to embodiments disclosed herein, a sample analyzing apparatus is provided in which an injector assembly injects a reagent onto a sample. The sample emits luminescent light in response to the reagent, which is transmitted to a detector. In some embodiments, the injector assembly is movable toward and away from the sample, which may be done in an automated manner using a driver. The injector assembly may include one or more needles that communicate with one or more reservoirs supplying reagent or other liquids. In some embodiments, the injector assembly further includes a light guide for communicating with the detector. In some embodiments, a cartridge may be provided in which the injector assembly, one or more reservoirs, and one or more pumps are disposed. The cartridge and/or the sample analyzing apparatus may be configured for enabling rinsing or priming to be done outside the apparatus. The cartridge and/or the apparatus sample analyzing may include one or more types of sensors configured for detecting, for example, the presence of liquid or bubbles in one or more locations of the sample analyzing apparatus and/or the cartridge.

Figure 1A:
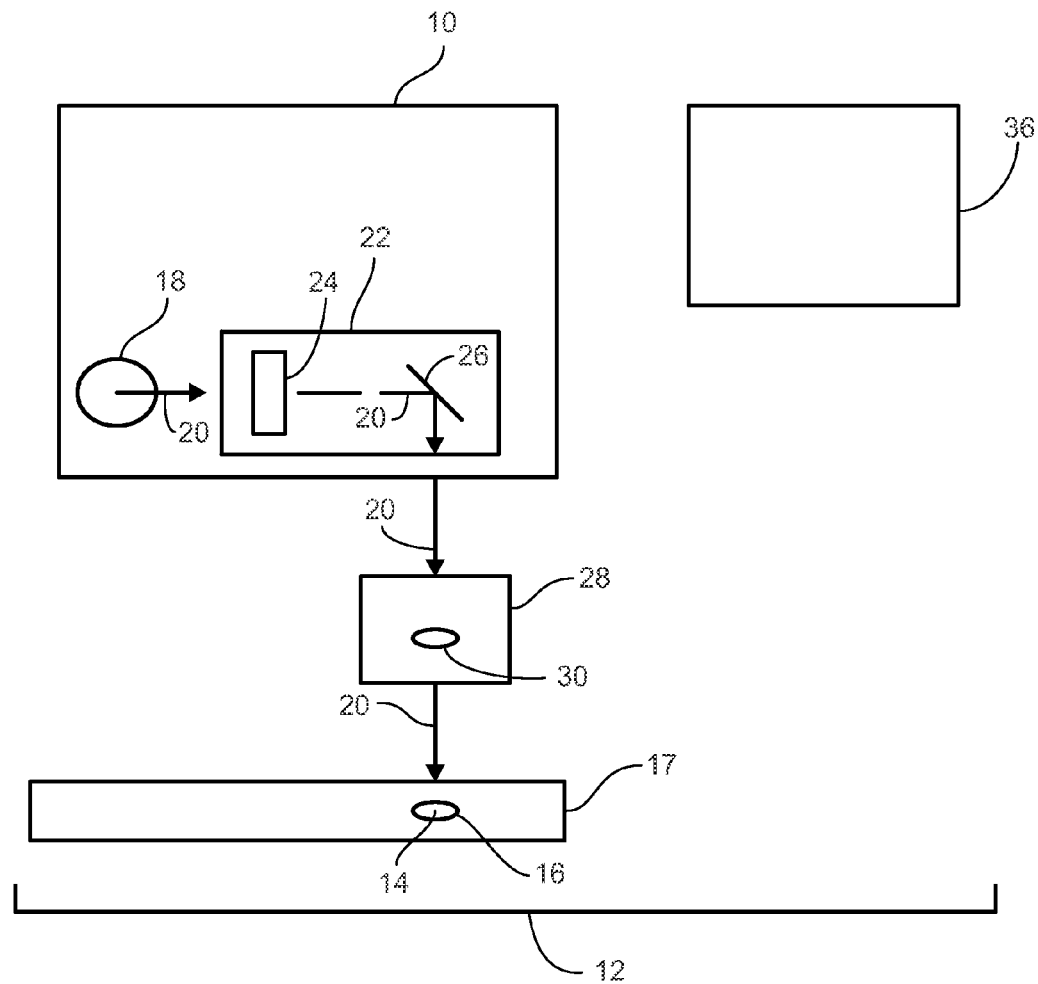
FIG. 1A is a schematic view of an example of components of a cartridge according to some embodiments.
Figure 1B:
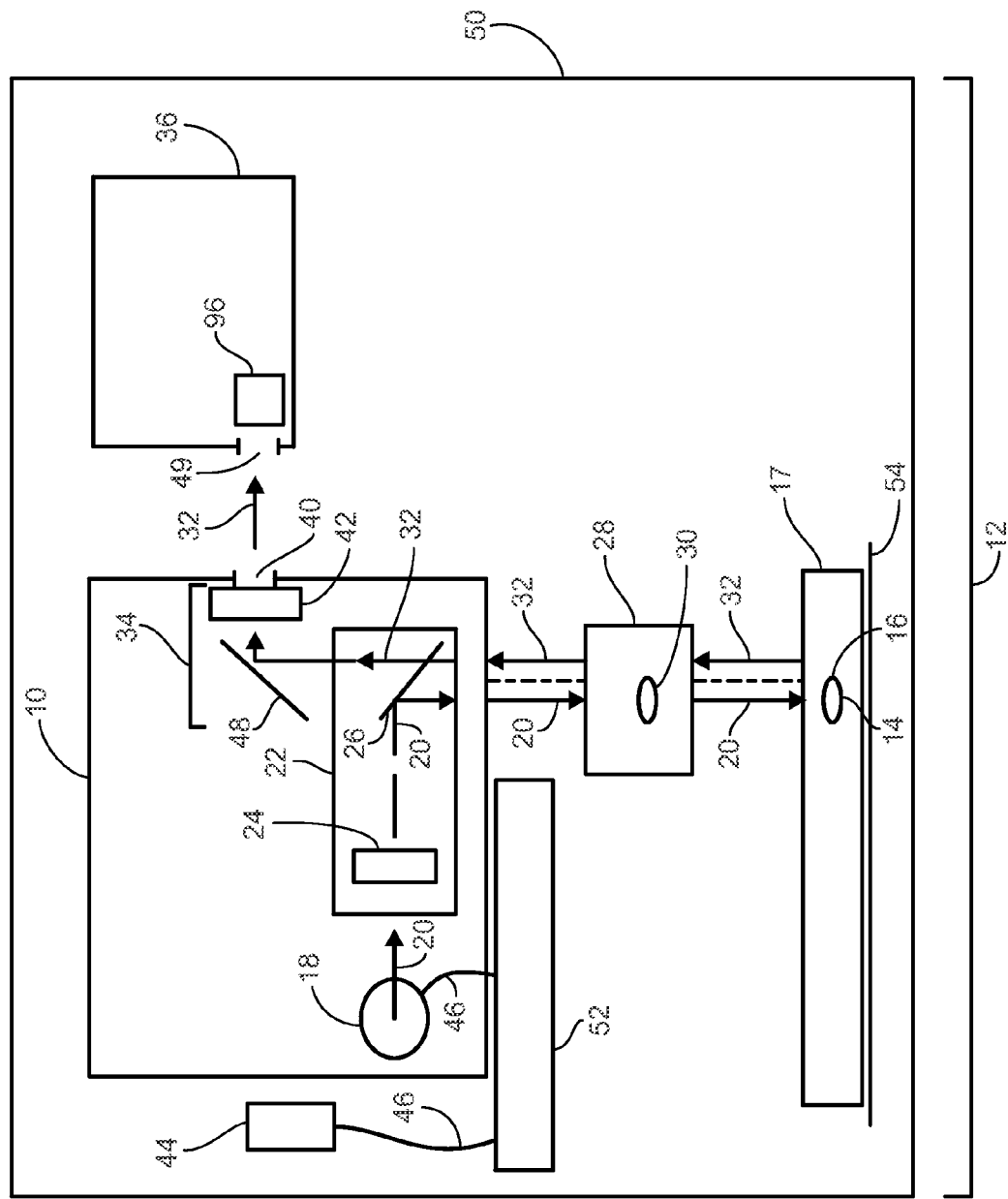
FIG. 1B is a schematic view of an example of components of a cartridge used for a fluorescence application according to some embodiments.
Figure 1C:
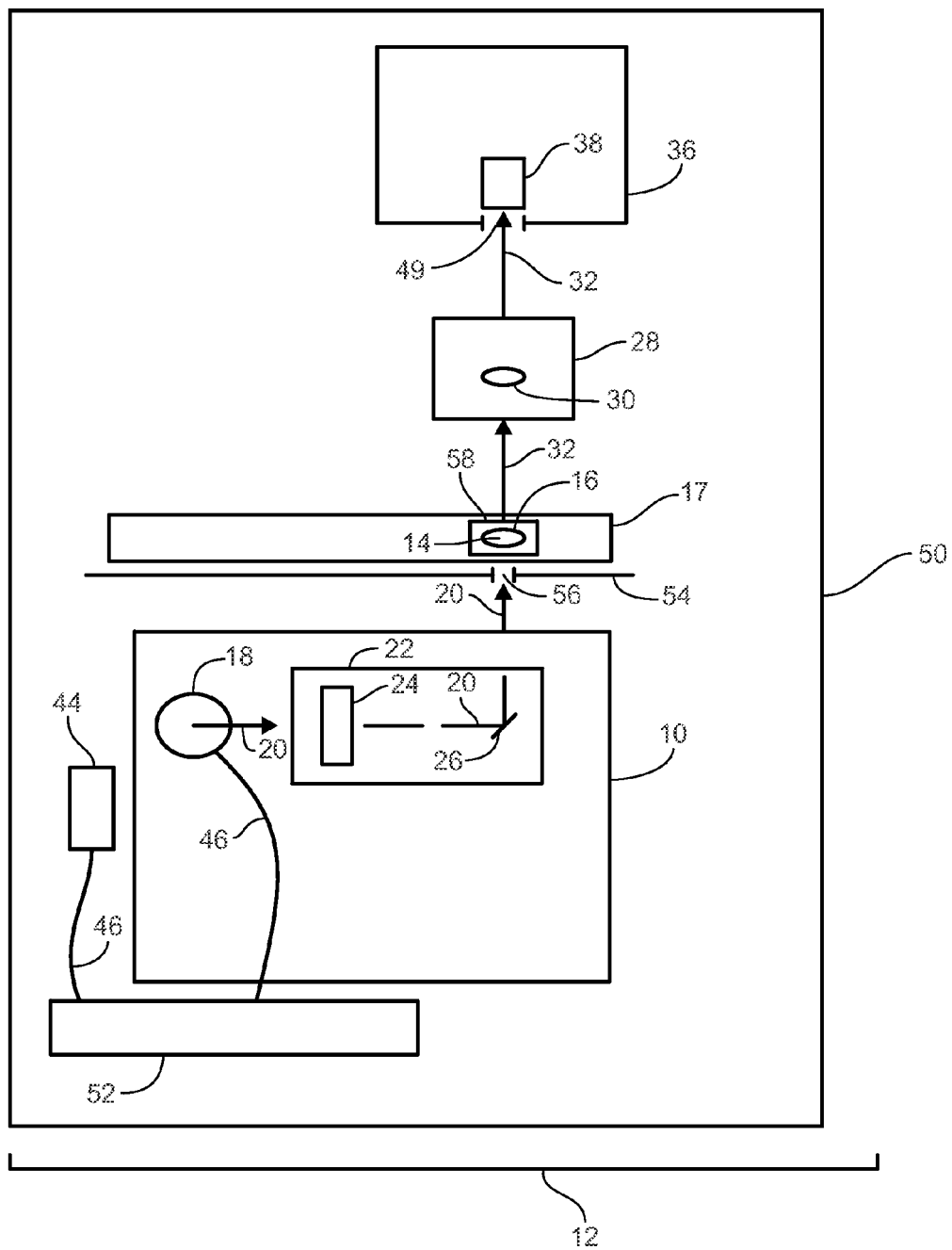
FIG. 1C is a schematic view of an example of components of a cartridge used for an absorbance application according to some embodiments.

Referring now to FIGS. 1A, 1B, and 1C a cartridge 10 for use in an apparatus 12 for analyzing a target 14 in a sample 16 is shown. The sample 16 may be held within the apparatus 12 on a sample support 17, such as a microplate. As shown in FIG. 1, the cartridge 10 comprises one or more light sources 18 that separately or in combination produce an exciting light 20. The cartridge 10 is designed to be removably engaged with the apparatus 12. The cartridge 10 has a first optical system 22 which has components for directing the exciting light 20 to the sample 16. The light source 18, such as a light emitting diode (LED) or a laser diode (LD), is collimated by lenses and apertures to emit a collimated beam of light. The first optical system 22 then transmits the exciting light 20 through filters 24, such as a bandpass filter, and then reflects the exciting light 20 out of the cartridge 10 with the help of a reflector 26, such as a dichroic beamsplitter, to a read head 28. The read head 28 directs the exciting light 20 toward the sample 16. The read head 28 contains an objective lens 30 that can be moved up and down. The objective lens 30 focuses the exciting light 20 onto the sample 16. The sample 16, containing the target 14, then produces an emitting light 32 (or emitted light 32), which is directed to an optical output detector 36, having a photomultiplier tube (PMT) 96, as shown in FIG. 1B, or a photodiode 38, as shown in FIG. 1C.

As also shown in FIGS. 1B and 1C the apparatus 12 is part of a system for analyzing a sample. The system comprises a structure 50, also referred to herein as a housing or apparatus housing, which is engaged (i.e., attached) to the read head 28, the detector 36, a power source 44, and a movable cartridge support 52. The movable cartridge support 52 positions the cartridge 10 within the apparatus 12 and is capable of supporting a plurality of cartridges and aligning each cartridge with the read head 28 and the detector 36. The cartridge 10 has a coupler 46 for providing a current supply from the power source 44 to the light source 18. In some embodiments, the cartridge 10 is mounted onto the support 52 and a plug terminating the electronics inside of the cartridge 10 is connected with a socket in the support 52. At the socket, several low voltage output lines of the power source 44 are available and interface lines with the main apparatus controller. The coupler 46 functions in connecting the cartridge 10 with other components in the apparatus 12, such as for receiving low DC voltage for the cartridge light source 18 and other electronics; establishing control lines for LED current adjustment; establishing control lines for cartridge recognition; data lines (e.g., an electronic bus) for detectors within the cartridge 10 (e.g., a photodiode for sending measured data to a controller); and synchronization lines for synchronizing pulses of the light source 18 with the data acquisition from detector(s) and other circuitry within the apparatus 12, such as photon counting circuitry in the main apparatus controller. In some embodiments, the coupler 46 is made from two parts, a printed circuit board that extends along the cartridge support 52, providing a socket for one or more cartridges 10, and a flexible flat cable at the end, bridging the gap to the main apparatus controller (flexible, because the cartridge support 52 can be moved). The electronic bus, or data line function is designed as of the type SPI (serial peripheral interface).

The system may also have a sample support carrier (or sample carrier) 54, such as a microplate scanning stage, attached to the structure for moving the sample support 17 either horizontally or vertically within the apparatus housing (e.g., structure 50).

Referring now to FIG. 1B, in certain embodiments, such as a cartridge 10 that is used for a fluorescence application, the emitting light 32 is collected from the target 14 by the read head 28 and collimated back into the cartridge 10. The cartridge 10 has a second optical system 34, which receives the emitted light 32 from the read head 28 and directs the emitted light 32 from the sample 16 to the detector 36. The emitting light 32 received from the read head 28 is transmitted through the reflector 26, and is then directed with a reflector 48 towards the cartridge exit 40, which interfaces with the detector 36 via a detector port 49. Before exiting the cartridge 10, the emitted light 32 is filtered through a filter 42, such as a bandpass filter, to reject contributions of excitation light being scattered back from the read head 28 and the sample 16. The entire path after the emitted light 32 has passed through the reflector 26 is optically shielded from those areas of the cartridge 10 which may be floated with diffuse scatter of exciting light 20.

Referring now to FIG. 1C, in certain embodiments, a cartridge 10, such as a cartridge that is used for an absorbance application, is positioned in the apparatus 12 in opposite to the detector 36. According to this embodiment, the exciting light 20 is transmitted through the sample 16 and sample support carrier 54 via an aperture 56 (i.e., a window or light transparent portion) in the sample support carrier 54 and an aperture 58 (i.e., a window or light transparent portion) in the sample support 17. Emitting light 32 from the target 14 is directed to the detector 36 (containing, e.g., a photodiode 38). The configuration of the cartridge 10 for measuring absorbance as shown in FIG. 1C is shown by way of example and other configurations are possible, for example, the cartridge 10 may be alternately positioned within the apparatus 12, such as in the same approximate plane as the detector 36 (e.g., side-by-side), and the emitting light 32 may be relayed to the detector 36, such as with a light guide, as will be understood by those of skill in the art with reference to this disclosure. In some embodiments, the absorbance cartridge 10 may be a dual wavelength absorbance cartridge or a wide band light source absorbance cartridge as further described in above-referenced U.S. Pat. No. 8,119,066.

The one or more light sources 18 housed in the cartridge 10 may be selected from suitable light sources known to those of skill in the art such as light emitting diodes (LEDs), laserdiodes, and a Xenon flash lamp module. In some embodiments, when the cartridge 10 is used for a fluorescence application, such as shown in FIG. 1B, the light source 18 is one or more LED light sources.

Figure 2:
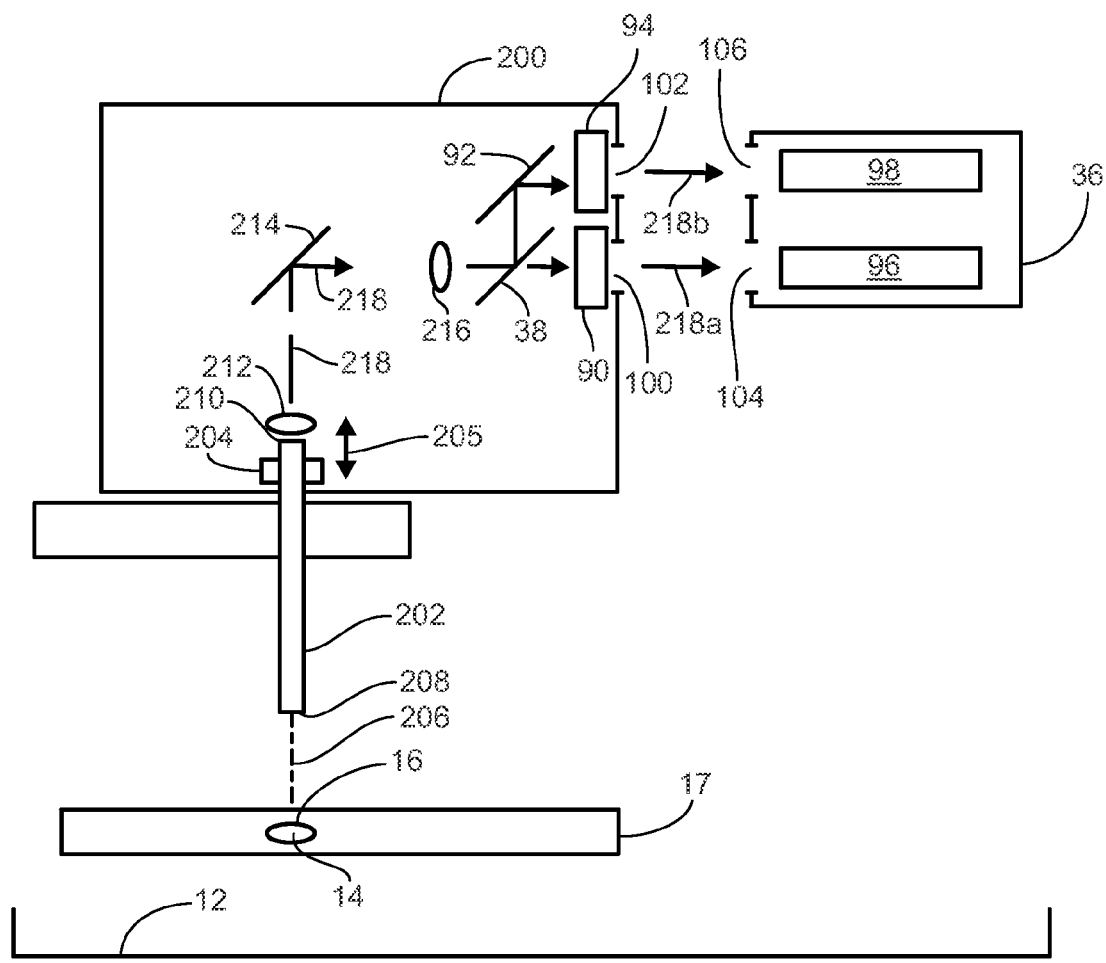
FIG. 2 is a schematic view of an example of a luminescence cartridge, having an integrated read head, according to some embodiments.

Referring now to FIG. 2, a luminescence cartridge 200 for use in an apparatus 12 for analyzing a target 14 in a sample 16 is shown. As shown in FIG. 2, the cartridge 200 comprises an integrated read head 202 and a driver 204, which moves the read head 202 in the direction indicated by arrow 205 into a detection position above the sample 16 when receiving emitting luminescent light 206 from the sample 16. The integrated read head 202 can also be moved by the driver 204 away from the sample 16 into a latent position when the luminescence cartridge 200 is not in use, or the apparatus 12 is being loaded with a new sample support 17. In some embodiments, the read head 202 is fully retractable into the cartridge 200. In some embodiments, for reasons of saving measurement time, the read head 202 will not move up and down when moving from the one sample 16 to the next, but will stay in proximity above the sample support 17, when moving from one sample 16 to the next sample. The integrated read head 202 is retracted when the sample support 17 is moved in or out of the apparatus 12 in order to avoid parts of the sample support carrier (not shown) that extend beyond the upper sample support level.

In some embodiments, the integrated read head 202 is a rigid light guide that receives emitting luminescent light 206 at a distal end 208 of the integrated read head 202 from a position above the sample holder 17 and sample 16. The emitting luminescent light 206 then exits the integrated read head 202 at a proximal end 210 of the integrated read head 202 and is collimated by a lens 212 to produce a collimated light beam 218.

According to an embodiment of the luminescence cartridge 200 shown in FIG. 2, the apparatus 12 and luminescence cartridge 200 may be configured for a bioluminescence resonance energy transfer (BRET) type measurement, where luminescence light is composed of two wavelength bands (e.g., a dual emission cartridge configuration) and which may be detected simultaneously with a dual channel detector. Examples of a dual emission cartridge and dual channel detector are further described in above-referenced U.S. Pat. No. 8,119,066. As shown in FIG. 2, the collimated emitting luminescent light beam 218 is redirected with a reflector 214 toward a dichroic beamsplitter 88 via a lens 216 and separated into two wavelength bands 218a and 218b. The first wavelength band 218a is passed or transmitted by a beamsplitter 88 toward the detector 36 via a first emission filter 90 (e.g., a bandpass filter). The second wavelength band 218b is reflected by the beamsplitter 88, and reflected at the mirror 92 toward the detector 36 via a second emission filter 94 (e.g., a bandpass filter). In some embodiments, the detector 36 is a dual channel detector having two detectors 96 and 98 (e.g., photomultiplier tubes) stacked to form the dual channel detector. In addition, the luminescence cartridge 200 has a dual exit port 100 and 102, which is aligned with the detectors 96 and 98 via detector ports 104 and 106.

In an alternative embodiment, for a wider class of luminescence measurements, which do not require simultaneous measurement of two wavelength bands, the cartridge 200 may be simplified by omitting the beamsplitter 88, mirror 92, and second emission filter 94.

Figure 3:
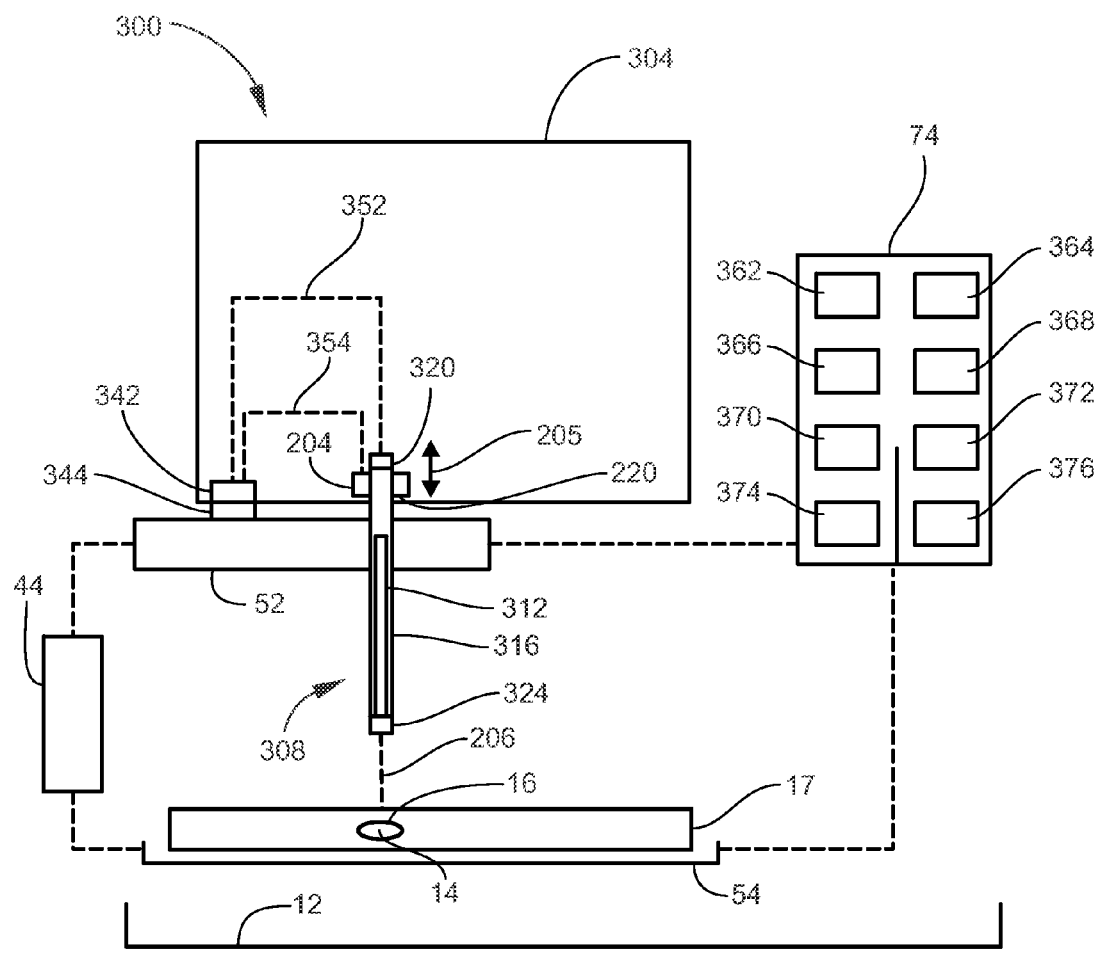
FIG. 3 is a schematic view of an example of a luminescence cartridge, having an integrated detector, according to some embodiments.

FIG. 3 is a schematic view of an example of a luminescence cartridge 300 according to another embodiment. The luminescence cartridge 300 may be utilized in conjunction with the apparatus 12 as a system for analyzing a target 14 in a sample 16. Like the cartridges described above and illustrated in FIGS. 1A-2, the luminescence cartridge 300 is designed to be removably engaged with the apparatus 12 by loading (mounting, installing) the luminescence cartridge 300 on the cartridge support 52, and may be replaced or exchanged with other cartridges of the same of different type.

The luminescence cartridge 300 includes a cartridge housing 304 that is sized and configured to be removably loaded or mounted on the cartridge support 52. The luminescence cartridge 300 also includes an integrated luminescence detector 308 that is movable through an opening 220 of the cartridge housing 304. In typical embodiments, the luminescence detector 308 is linearly movable in a reciprocating manner as indicated by an arrow 205, i.e., alternately toward the cartridge housing 304 (and thus away from the sample carrier 54) to selected retracted positions and away from the cartridge housing 304 (and thus toward the sample carrier 54) to selected extended positions. Depending on the design and location of the cartridge support 52, the cartridge support 52 may also include an opening to accommodate the extension of the luminescence detector 308 toward the sample carrier 54. To actuate and control the movement of the luminescence detector 308, the luminescence cartridge 300 includes a detector driver (or drive mechanism, or drive assembly) 204 that is coupled to the luminescence detector 308. The detector driver 204 may be mounted at the cartridge housing 304 in any suitable manner, and in typical embodiments is contained within the interior of the cartridge housing 304. As appreciated by persons skilled in the art, the detector driver 204 may have any configuration suitable for moving (i.e., retracting and extending) the luminescence cartridge 300 to any selected position relative to the cartridge housing 304 (and thus relative to the sample carrier 54 and any selected sample 16 supported by the sample carrier 54). In a typical embodiment, the detector driver 204 includes a motor (e.g., a micromotor) coupled to a linkage or transmission that is in turn coupled to the luminescence detector 308. The detector driver 204 may include bearings or other appropriate components necessary for facilitating reliable and accurate actuation of the luminescence detector 308. The linkage or transmission may have any configuration suitable for converting the rotational movement of the motor to linear movement of the luminescence detector 308. For example, the linkage or transmission may include a set of gears such as a rack and pinion, a set of bevel gears, a worm and worm gear, etc.

To facilitate loading of luminescence cartridge 300 on the cartridge support 52 and subsequent removal therefrom, and to prevent damage to the luminescence detector 308 during loading and removal, the luminescence detector 308 may be fully retractable within the cartridge housing 304 by the detector driver 204 such that no part of the luminescence detector 308 extends outside of the cartridge housing 304. The luminescence detector 308 may also be moved to the fully retracted position while the cartridge support 52 is moving the luminescence detector 308 (and any other cartridges loaded on the cartridge support 52) to different positions within the apparatus housing 50. However, the luminescence detector 308 typically does not to be moved when acquiring luminescence data from multiple samples 16. That is, as noted elsewhere multiple samples 16 may be provided at individual sites of a sample support 17, such as in different wells of a multi-well plate that is supported on the sample carrier 54. The luminescence detector 308 may be moved to a desired distance from the first sample 16 which, in the illustrated "top reading" example, is a desired elevation above the first sample 16. This desired distance will typically be the same for all samples 16 contained on the sample support 17. Thus, the position of the luminescence detector 308 typically does not need to be adjusted as the sample carrier 54 moves the sample support 17 to sequentially align one sample 16 after another with the luminescence detector 308 to take sequential luminescence readings.

In the illustrated embodiment, the luminescence detector 308 is generally elongated between a proximal end and a distal end. In typical embodiments, the luminescence detector 308 is cylindrical with a circular cross-section, although in other embodiments may have a polygonal (e.g., rectilinear) cross-section. As an example, the luminescence detector 308 may have a length of 75 mm and an outer diameter of 11 mm. It will be understood, however, that this example is not limiting and the luminescence detector 308 may have any size suitable for use with the luminescence cartridge 300 and associated apparatus 12. The distal end (or optical output end) serves as the optical input of the luminescence detector 308 at which luminescent light 206 emitted from the sample 16 is received. The proximal end in typical embodiments remains in the cartridge housing 304 throughout the extent of travel of the luminescence detector 308.

The luminescence detector 308 includes an active detector component 312 that receives the luminescent light 206 via the optical input.

An advantage of integrating the luminescence detector 308 with the cartridge housing 304, as opposed to utilizing the output detector 36 located external to the luminescence cartridge 300 (as in, for example, FIG. 2), is that it enables the luminescence detector 308 to be configured for dedicated operation in conjunction with luminescence measurements. That is, unlike the externally located output detector 36, the integrated luminescence detector 308 does not need to accommodate the operation of any other removable cartridge that might be loaded in the apparatus 12. Because the luminescence detector 308 is not utilized for a broader variety of data acquisitions (e.g., absorbance, fluorescence), the configuration of the luminescence detector 308 may be optimized for operation specifically with luminescence measurements. Thus, for example, the luminescence detector 308 may be selected to have maximum sensitivity to the wavelength ranges typically associated with the luminescent light 206. As an example, the wavelength of the luminescent light 206 may range from visible wavelengths to about 800 nm.

Examples of suitable detector components 312 include, but are not limited to, photomultiplier tubes (PMTs) and photodiodes. For many applications, a PMT may be considered to be a preferred type of detector component 312 in view of its relatively low cost, high gain, high frequency response, large numerical aperture, and capability for single photon counting. As appreciated by persons skilled in the art, the PMT typically includes a series of electrodes enclosed in an evacuated glass tube, for example a photocathode located at the optical input end of the tube, followed by a series of dynodes, and followed by an anode. One or more focusing electrodes may be located between the photocathode and the first dynode. The anode is in signal communication with an electrical connector located at the output end of the glass tube, typically via a sealed electrical feed-through structure. In the illustrated embodiment, the luminescence detector 308 also includes an outer detector housing 316 that encloses and thus protects the detector component 312. The detector housing 316 provides a robust structure to which the detector driver 204 may be directly coupled.

At the proximal end, the luminescence detector 308 may include an electrical connector 320 (e.g., contacts, terminals, pins, wire support, etc.), which may be part of or mounted to the detector housing 316. The detector component 312 is in signal communication with the electrical connector 320 to enable measurement signals generated by the luminescence detector 308 to be outputted to signal processing circuitry (e.g., data acquisition circuitry) located external to the luminescence cartridge 300. In some embodiments, the detector component 312 may be about as long as the detector housing 316 such that the electrical connector of the detector component 312 is in direct contact with (or is the same as) the illustrated electrical connector 320.

In some embodiments, the luminescence detector 308 may include an adjustable iris (or iris assembly) 324 mounted to the detector housing 316 at the distal (optical input) end. The adjustable iris 324 may have any configuration suitable for adjusting the numerical aperture of the luminescence detector 308, and thus the range of angles over which the luminescence detector 308 can receive the luminescent light 206 emitted from the sample 16. The adjustable iris 324 is thus useful for maximizing the amount of luminescent light 206 received from the target sample 16 and for minimizing the stray light received from adjacent samples 16 (e.g., samples 16 in adjacent wells of a multi-well plate). The adjustable iris 324 is also useful for accommodating different types and geometries of sample supports 17, for example different multi-well plate formats (e.g., 96-well, 384-well, 1536-well, etc.), thereby ensuring that light input is optimized for different sample supports 17. Adjustment of the iris 324 may also be done in combination with adjustment of the distance of the optical input end of the luminescence detector 308 from the sample 16 to optimize light input. Various types of adjustable irises 324 are known to persons skilled in the art. As an example, the adjustable iris 324 may include a set of overlapping shutters (not shown) that are movable relative to each other to define an opening of variable diameter through which the luminescent light 206 passes into the luminescence detector 308. The adjustable iris 324 may also include an actuating device (not shown) that moves the shutters. The actuating device may be manual or automated. An automated actuating device may be in signal communication with the electrical connector 320 of the detector housing 316 to receive power from the power source 44.

As indicated earlier in this disclosure, loading removable cartridges at the cartridge support 52 may entail coupling the removable cartridges with the cartridge support 52 in such a way as to place certain components of the removable cartridges in signal communication with the power source 44 and/or the electronic controller (or system controller, or main apparatus controller) 74, as appropriate. As an example, schematically illustrated in FIG. 3, the luminescence cartridge 300 includes a first electrical connector 942 and the cartridge support 52 includes a second electrical connector 944. The luminescence cartridge 300 may be removably engaged with the cartridge support 52 by removably engaging or coupling the first electrical connector 942 with the second electrical connector 944. For this purpose, the first electrical connector 942 and the second electrical connector 944 may have any suitable complementary configurations (e.g., plugs and sockets, male and female connectors, etc.). The detector component 312, and the adjustable iris 324 if provided and if powered, may communicate with the first electrical connector 942 via one or more wires or a ribbon cable 952. The wire(s) or ribbon cable 952 should be of sufficient length to accommodate the travel of the luminescence detector 308 within the cartridge housing 304. The detector driver 204 may likewise communicate with the first electrical connector 942 via a wire 954. The second electrical connector 944 in turn communicates with the power source 44 and the system controller 74, as schematically indicated by respective dashed lines interconnecting the cartridge support 52 with the power source 44 and the system controller 74. The dashed lines may represent any suitable communication link (wired or wireless). By this configuration, installing the luminescence cartridge 300 at the cartridge support 52 may place the detector driver 204 and adjustable iris 324 in signal communication with the power source 44 and the system controller 74, and the detector component 312 in signal communication with the system controller 74, all via the coupling made between the first electrical connector 942 and the second electrical connector 944. Additional dashed lines in FIG. 3 depict communication between the power source 44 and the cartridge support 52 and the sample carrier 54, and between the system controller 74 and the cartridge support 52 and the sample carrier 54.

As also schematically illustrated in FIG. 3, the system controller 74 may represent one or more modules configured for controlling, monitoring and/or timing various functional aspects of the apparatus 12 and the luminescence cartridge 300 and/or for receiving data or other signals from the apparatus 12 and the luminescence cartridge 300. In typical embodiments, the system controller 74 a main electronic processor 362 providing overall control, and may include one or more electronic processors configured for dedicated control operations or specific signal processing tasks. The system controller 74 may also include one or more memories and/or databases 364 for storing data and/or software. The system controller 74 may also include a computer-readable medium 366 that includes instructions for performing any of the methods disclosed herein. The functional modules of the system controller 74 may comprise circuitry or other types of hardware (or firmware), software, or both. In the illustrated example, the modules may include one or more of the following: signal processing (or data acquisition) circuitry 368 for receiving measurement signals from the luminescence detector 308, a detector drive controller 370 for controlling the movement of the luminescence cartridge 300, an iris controller 372 for controlling the adjustment of the iris 324, a cartridge support drive controller for controlling the movement of the cartridge support 52, and a sample carrier drive controller for controlling the movement of the sample carrier 54. The system controller 74 may also be representative of one or more types of user interface devices, such as user input devices (e.g., keypad, touch screen, mouse, and the like), user output devices (e.g., display screen, printer, visual indicators or alerts, audible indicators or alerts, and the like), a graphical user interface (GUI) controlled by software, and devices for loading media readable by the electronic processor (e.g., logic instructions embodied in software, data, and the like). The system controller 74 may include an operating system (e.g., Microsoft Windows® software) for controlling and managing various functions of the system controller 74.

In one embodiment of a method for analyzing a target 14 in a sample 16, the luminescence cartridge 300 is loaded (or installed) on the cartridge support 52 to position the luminescence cartridge 300 in the apparatus housing 50 (FIG. 1B). Loading may include opening a panel or door of the apparatus 12 (such as may be located on a side of the apparatus housing 50) to access the cartridge support 52. The cartridge support 52 may first be moved to a position at least partially outside the apparatus housing 50, and after the luminescence cartridge 300 is loaded on the cartridge support 52, the cartridge support 52 may then be moved back into the apparatus housing 50 with the luminescence cartridge 300 loaded thereon. Loading may also entail coupling the first and second electrical connectors 342 and 344 as described above to establish paths for transmitting power, data and control signals. Before or after loading the luminescence cartridge 300, the sample 16 is loaded on the sample carrier 54, typically by first loading the sample 16 on a sample support 17 and in turn loading the sample support 17 on the sample carrier 54. A plurality of samples 16 may be loaded together on an appropriate sample support 17 such as a multi-well plate. Ultimately, the cartridge support 52 and the sample support 17 will be positioned relative to each other such that the sample 16 will be aligned with the luminescence detector 308, either above or below the luminescence detector 308 depending on the configuration. In the present context, "aligned" means optically aligned, i.e., positioned so as to establish an optical path sufficient for luminescence data acquisition from the sample 16.

The luminescence detector 308 is then moved toward the sample 16 until its optical input end reaches a desired distance (reading position) from the sample 16. An advantage of the integrated luminescence detector 308 is it may be moved very close to the sample 16 to be interrogated, thus maximizing light collection from the target sample 16 and minimizing stray light collection from adjacent samples. In some embodiments, the luminescence detector 308 is equipped with an iris 324 that may be adjusted as needed in preparation for data acquisition. At the reading position, the luminescence detector 308 receives (collects) the luminescent light 206 emitted from the sample 16. The luminescence detector 308 converts these optical signals into electrical signals (detector signals, or measurement signals) and transmits the electrical signals to the signal processing circuitry 368 of the system controller 74. In the case of multiple samples 16, the sample carrier 54 may be moved to sequentially align each additional sample 16 with the luminescence detector 308, whereby luminescence measurements are taken from all samples 16 sequentially.

At the completion of making the luminescence measurements, the luminescence cartridge 300, being a modular or removable cartridge as described throughout the present disclosure, may then be removed from the cartridge support 52, and thereafter replaced with another luminescence cartridge 300 or different type of removable cartridge as desired. Before moving the cartridge support 52 through the apparatus housing 50 as needed to remove the luminescence cartridge 300, the luminescence detector 308 may be retracted to a position completely inside the cartridge housing 304 to protect the luminescence detector 308 during movement.

The luminescence cartridges 200 and 300 described above may be utilized in various types of luminescence measurement techniques, including glow luminescence and flash luminescence. These types of measurements may be applied, for example, in conjunction with apoptosis studies, cAMP (cyclic adenosine monophosphate) quantitation, GPCR (G protein-coupled receptor) ligand binding, and immunoassaying. Glow luminescence reagents (e.g., luciferase, luciferin) may be added to samples 16 before or after loading the sample support 17 on the sample carrier 54 and moving the sample carrier 54 into the apparatus housing 50. Dispensing devices suitable for controllably adding glow luminescence reagents to samples 16 are generally understood by persons skilled in the art, and may be manually operated or automated devices. A dispensing device may be a component of the apparatus 12, in which case it may be controlled by the system controller 74, or it may be a device separate from the apparatus 12. Flash luminescence reagents (e.g., aequorin or other photoprotein) may be dispensed by an injector provided with the apparatus 12 or an injector integrated with a removable cartridge. Examples of the use of luminescence cartridges 200 and 300 for flash luminescence are described below in conjunction with FIG. 8.

Figure 4:
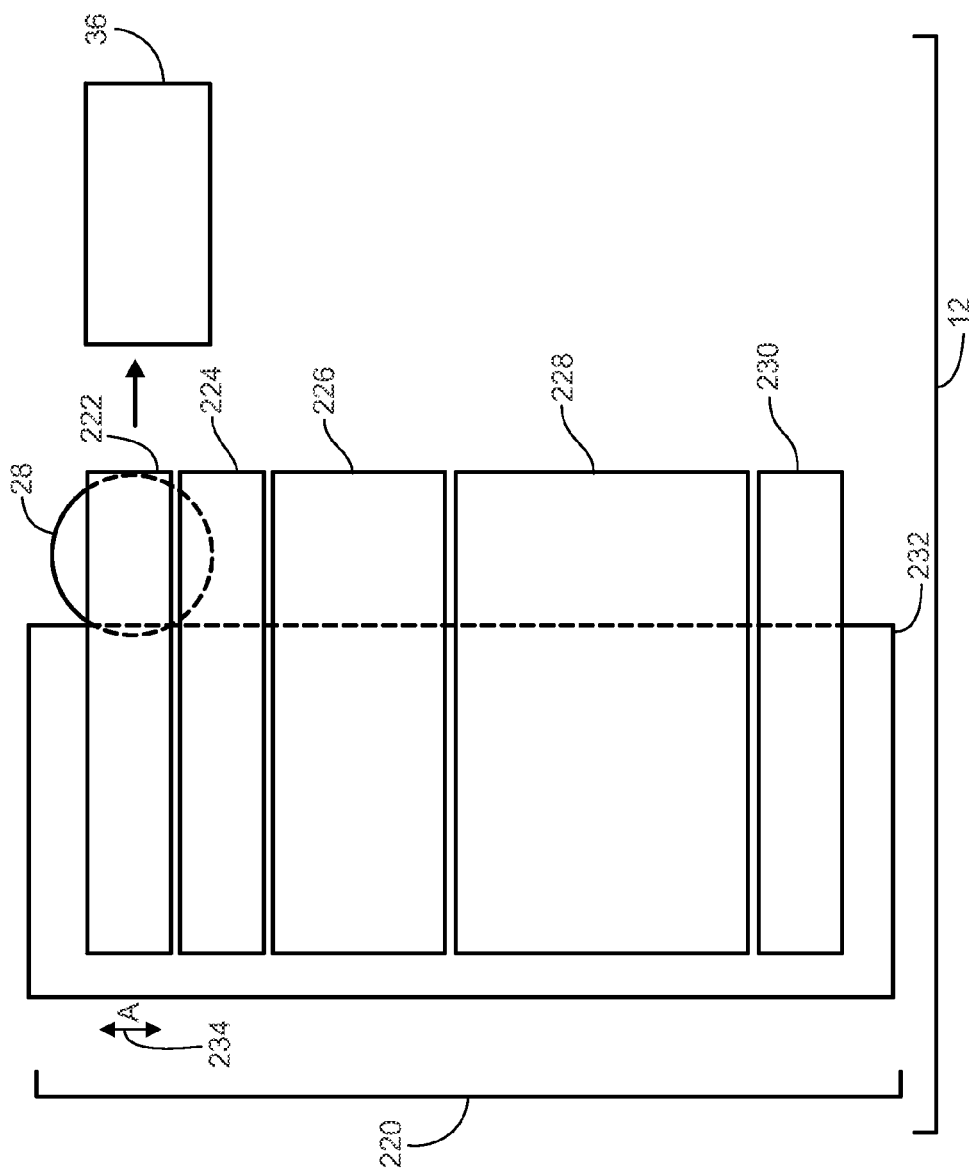
FIG. 4 is a schematic top view of an example of a cartridge system according to some embodiments.

Referring now to FIG. 4, another embodiment of the invention, a cartridge system 220 for use in an apparatus 12 for analyzing a target in a sample (not shown) is provided. As shown in FIG. 4, the apparatus 12 has a cartridge support 232 (i.e., a slide mechanism or cartridge slider) which is configured to concurrently receive a multitude of different cartridges. According to this embodiment, a cartridge for a desired application, such as fluorescence, absorbance, or luminescence, is selected by the user and is selectively aligned by the apparatus 12 with the read head 28 and the output detector 36 by moving the selected cartridge into the analysis position A, along the direction indicated by arrow 234. In this manner, a single instrument may house several application cartridges at a time and an application may be selected by the user without the user performing a multitude of application specific adjustments to the instrument such as selecting the correct combination and adjustment of filters, beamsplitters, apertures, and lightguides, etc. for a given application.

Referring again to FIG. 4, the cartridge system 220 comprises a plurality of cartridges, each cartridge being removably engaged with the apparatus 12. Examples of cartridges that may be used in the cartridge system 220 may include one or more of the cartridges described herein. Exemplary cartridges used in the cartridge system 220 are shown in FIG. 4 as cartridge 222, cartridge 224, cartridge 226, cartridge 228, and cartridge 230. However, a greater or fewer number of cartridges may be used in the cartridge system 220 and the cartridges need not have the same dimensions such that cartridges having more complex systems (and larger dimensions) or less complex systems (and smaller dimensions) may be used in the apparatus 12. The apparatus 12 has a cartridge support 232 (i.e., a slide mechanism or cartridge slider) which is configured to receive the cartridges (e.g., cartridges 222, 224, 226, 228, and 230) and align each of the cartridges with the detector 36 and read head 28.

In some embodiments, each cartridge has indicia, such as an electrically erasable programmable read-only memory, EEPROM, that indicates the type of detection that the cartridge can be used for and the corresponding parameters for the particular cartridge. In some embodiments, the cartridge support 232 features a cartridge detector, such as a data line function, or an electronic bus system, that enables the instrument control software (not shown) to identify a cartridge's slot position (i.e., the position of the cartridge on the cartridge support 232) and recognize any application specific parameters stored in the cartridge's EEPROM.

In some embodiments, the cartridge support 232 dimensions are such that it can be moved through a front door or access panel of the apparatus housing and every cartridge position or "slot" on the cartridge support 232 can be accessed for installation or removal of a cartridge. In some embodiments, one cartridge is capable of being removed from the cartridge support 232 and exchanged with a second cartridge, or alternately, a new cartridge is installed in an empty slot on the cartridge support 232 without the use of mechanical tools, or with a simple mechanical tool, such as for releasing a fastening mechanism (e.g., a fastening clip).

In some embodiments, at least one of the cartridges in the cartridge system 220 has one or more light sources that produces an exciting light, such as certain cartridges described herein. In some embodiments, at least one of the cartridges in the cartridge system 220 has an integrated read head and a driver (not shown) for moving the read head, such as certain cartridges described herein. In some embodiments, at least one of the cartridges in the cartridge system 220 is a luminescence cartridge such as described herein.

Figure 5:
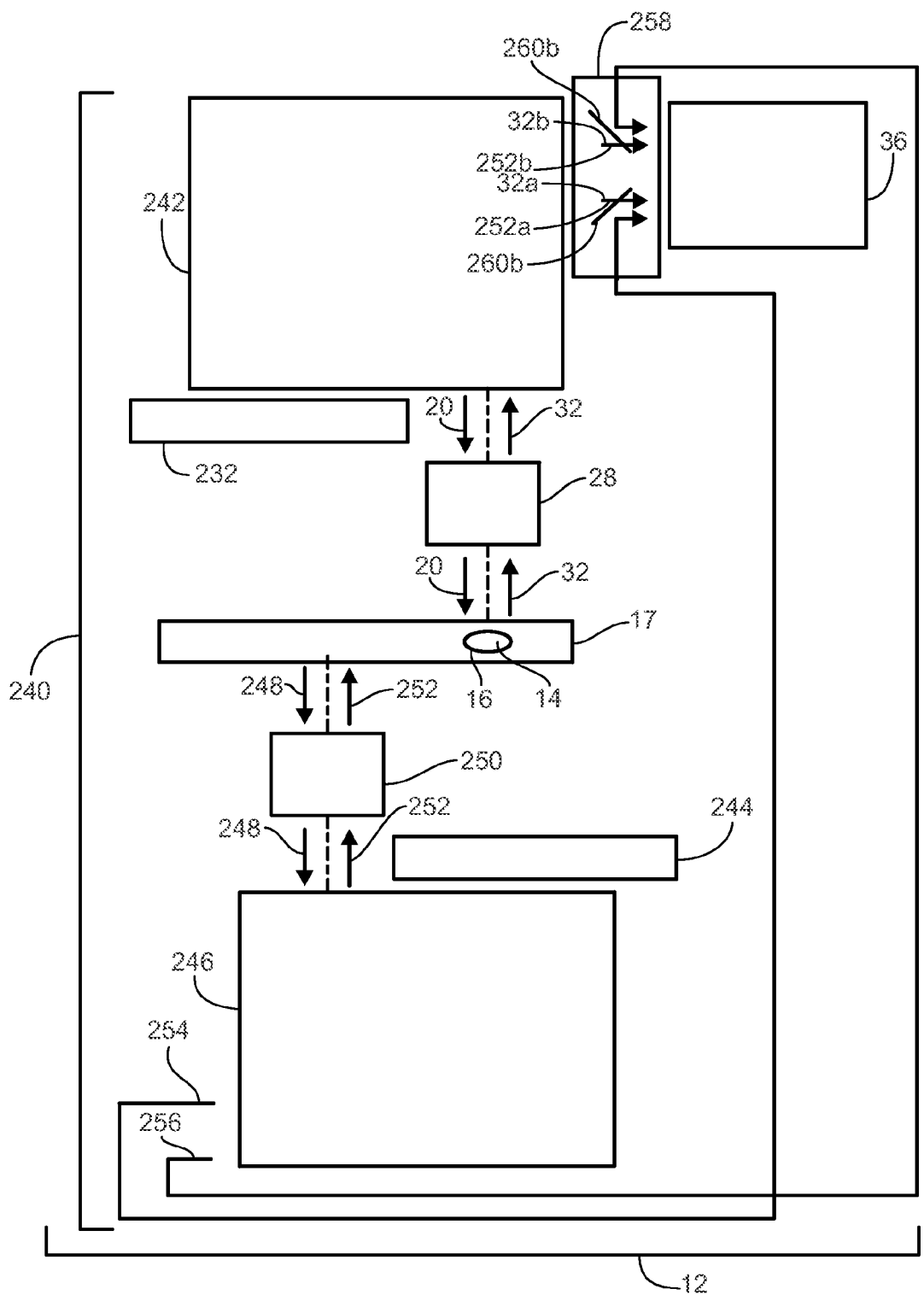
FIG. 5 is a schematic view of an example of a top and bottom reading cartridge system according to some embodiments.

Referring now to FIG. 5, in another embodiment, a top and bottom reading cartridge system 240 for use in an apparatus 12 for analyzing a target 14 in a sample 16 is provided. As shown in FIG. 5, the apparatus 12 has a first cartridge support 232 which supports a first cartridge 242 and a second cartridge support 244 which supports a second cartridge 246. The first and second cartridges 242 and 246 may be any of those described herein. As noted above in the description relating to FIGS. 1B and 1C, the first cartridge support 232 and/or the second cartridge support 244 may be configured for supporting a plurality of cartridges, and for selectively aligning one or more of the cartridges with the read head 28 or 250 and/or the detector 36, as appropriate for carrying out a particular type of measurement.

According to the embodiment shown in FIG. 5, the first cartridge support 232 and first cartridge 242 are positioned above the sample support 17. The exciting light 20 from the first cartridge 242 is directed to the sample 16 through a first read head 28. The emitting light 32 from the sample 16 is then directed again through the first cartridge 242, by which the emitting light 32 is directed to the detector 36 as previously described herein, and/or as described in above-referenced U.S. Pat. No. 8,119,066. The emitting light 32 may be split into one or more wavelength bands 32a and 32b as previously described. The second cartridge support 244 and second cartridge 246 are positioned below the sample support 17 and the exciting light 248 from the second cartridge 246 is directed to the sample 16 through a second read head 250. The emitting light 252 is then directed again through the second cartridge 246, where it is split into emitting lights 252a and 252b and relayed remotely to the detector 36. In some embodiments, light guides 254 and 256 relay the emitting light 252a and 252b from the bottom of the second cartridge 246 through an exit port (not shown) to the detector 36.

In some embodiments, a luminescence cartridge 200 or 300 such as described above and illustrated in FIG. 2 or 3 is loaded at the first cartridge support 232 and thus above the sample support 17 for top reading, or is loaded at the second cartridge support 244 and thus below the sample support 17 for bottom reading, or two luminescence cartridges 200 or 300 may be respectively loaded at the first cartridge support 232 and second cartridge support 244.

The design of the first and second cartridges 242 and 246 is independent of whether the cartridge is positioned either above or below the sample support 17. However, when the cartridge configuration shown in FIG. 5 is used, a movable detector port support 258 (e.g., a slide or selector wheel mechanism) is used which switches the detector 36 from seeing either emitting light 32a and 32b from the first cartridge 242 and first read head 28 or seeing emitting light 252a and 252b from the second cartridge 246 and second read head 250. The emitting light 252a and 252b exiting the light guides 254 and 256 is reflected into the detector 36 by mirrors 260a and 260b. The selection between the first and second cartridges 242 and 246 is done by moving the movable detector port support 258 along an axis 262 perpendicular to the detector 36. This embodiment is further detailed in FIG. 6.

Figure 6:
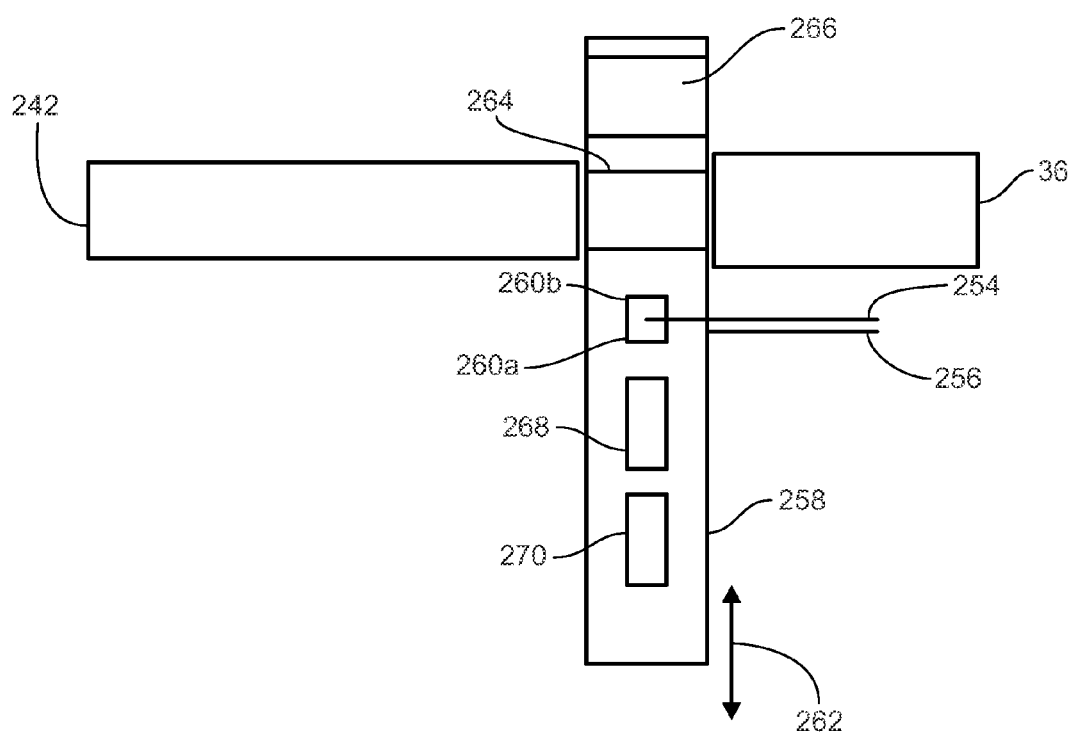
FIG. 6 is a schematic top view of the cartridge configuration shown in FIG. 5.

According to the embodiment shown in FIG. 6, the movable detector port support 258 is located in the gap between the exit of the first cartridge 242 and the entrance to the detector 36. The movable detector port support 258 houses an aperture 264 (e.g., a beam pass) which directs emitting light 32a and 32b from the first cartridge 242 and a beam stop/shutter 266 which protects the detector 36 when the instrument front door is opened, such as for maintenance or to exchange a cartridge. The movable detector port support 258 may also be equipped with light attenuating filters 268 and 270 which enable the system to analyze a signal that is too strong for the detector 36. The movable detector port support 258 may also be equipped with a constant low power light source in order to monitor the function and performance of the detector 36 over longer periods of operation (not shown). The light source resident in the detector port support 258 may be built from a LED and stabilized by feedback from a photodiode, as described in above-referenced U.S. Pat. No. 8,119,066. The LED output is attenuated down to levels acceptable to the detector 36 by help of a diffusing glass. Another position along the movable detector port support 258 may house mirrors 260*a* and 260*b* that reflect the emitting light 252*a* and 252*b* exiting the light guides 256 and 254 from above and below the movable detector port support 258. Emitting light 252*a* and 252*b* exiting the light guides 256 and 254 can enter the detector 36 when the position of the light guides 256 and 254 on the detector port support 258 is aligned with the detector 36.

Figure 7:
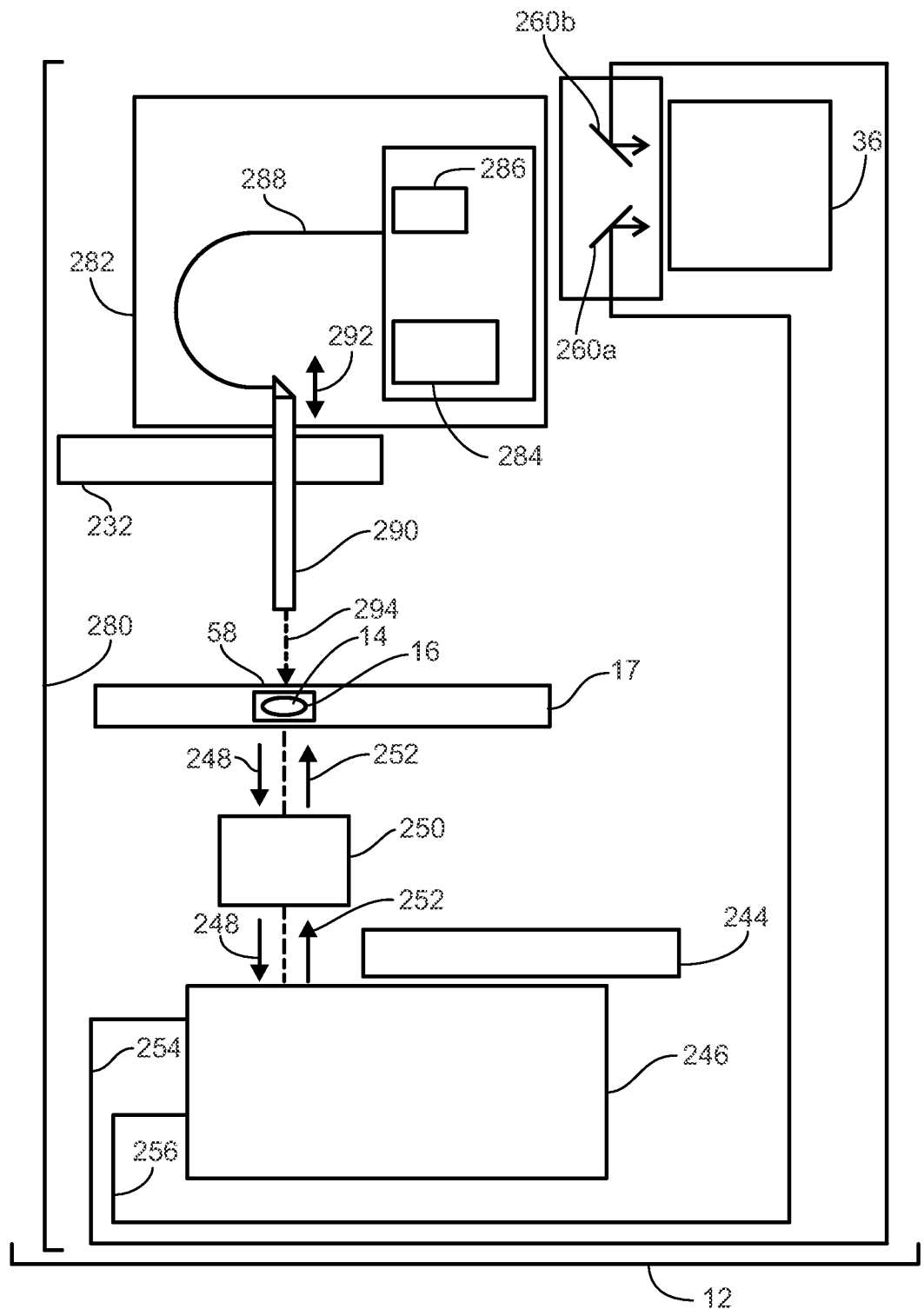
FIG. 7 is a schematic view of an example of a flash fluorescence cartridge system according to some embodiments.

Referring now to FIG. 7, another embodiment of the invention, a flash fluorescence cartridge system 280 for use in an apparatus 12 for analyzing a target 14 in a sample 16 is provided. The flash fluorescence cartridge system 280 has an injector cartridge (i.e., the first cartridge 282) that may be used for flash fluorescence applications, which require injection of a starter reagent in combination with immediate fluorescence reading.

For typical flash fluorescence applications, clear bottom microplates are frequently used as the sample support 17 (i.e., a sample support having an aperture 58) such that injection of the reagent occurs from above the well and fluorescence is measured simultaneously from below the sample holder 17. Accordingly, FIG. 7 uses the top and bottom reading cartridge configuration, which has been described with respect to FIG. 5. According to the embodiment shown in FIG. 7, an injector cartridge 282 is installed as the first cartridge (i.e., the upper cartridge) on the first cartridge support 232. A second cartridge 246 is positioned on a second cartridge support 244. The second cartridge 246 may be any of those described herein such as certain cartridges described herein and/or in above-referenced U.S. Pat. No. 8,119,066, but configured for a fluorescence application. As noted again, the first cartridge support 232 and/or the second cartridge support 244 may be configured for supporting a plurality of cartridges, and for selectively aligning one or more of the cartridges with the read head 250 and/or the detector 36, as appropriate for carrying out a particular type of measurement.

As shown in FIG. 7, the first cartridge 282 features a reagent reservoir 284, a pump 286, and a tubing system 288 connected to a nozzle 290 (which may be rigid). The nozzle 290 can be driven down from within the first cartridge 282 to approach the sample support 17 from above, as shown by arrow 292. The nozzle 290 is aligned with a sample 16 and read head 250 and reagent 294 is delivered to the sample 16 via the nozzle 290. Exciting light 248 and emitting light 252 is directed to the sample 16 and subsequently to the detector 36 as described with respect to FIG. 5. Sample measurement may take place before, during, and after injection of reagent 294.

Using an injector module that can be easily removed under routine operating conditions, such as the injector cartridge described herein, provides several advantages. The injector cartridge and external docking station may also be used as a precision dispenser apparatus. In addition, the cartridge's tubing system can be easily rinsed/cleaned by the customer and primed, i.e., floated, thereby removing bubbles, with the reagent outside of the instrument enclosure. This may occur with the injector cartridge still plugged into the cartridge support, but with the cartridge support moved through the instrument door and having a waste reservoir placed underneath. Priming may also occur with the injector cartridge removed from the cartridge support and plugged into a docking station. Both strategies reduce the risk of accidentally floating the interior of the apparatus with reagent. Also, the output of the injector cartridge can be calibrated for the customer's solvents at the customer site using an external docking station mounted on top of weighing scales.

Figure 8:
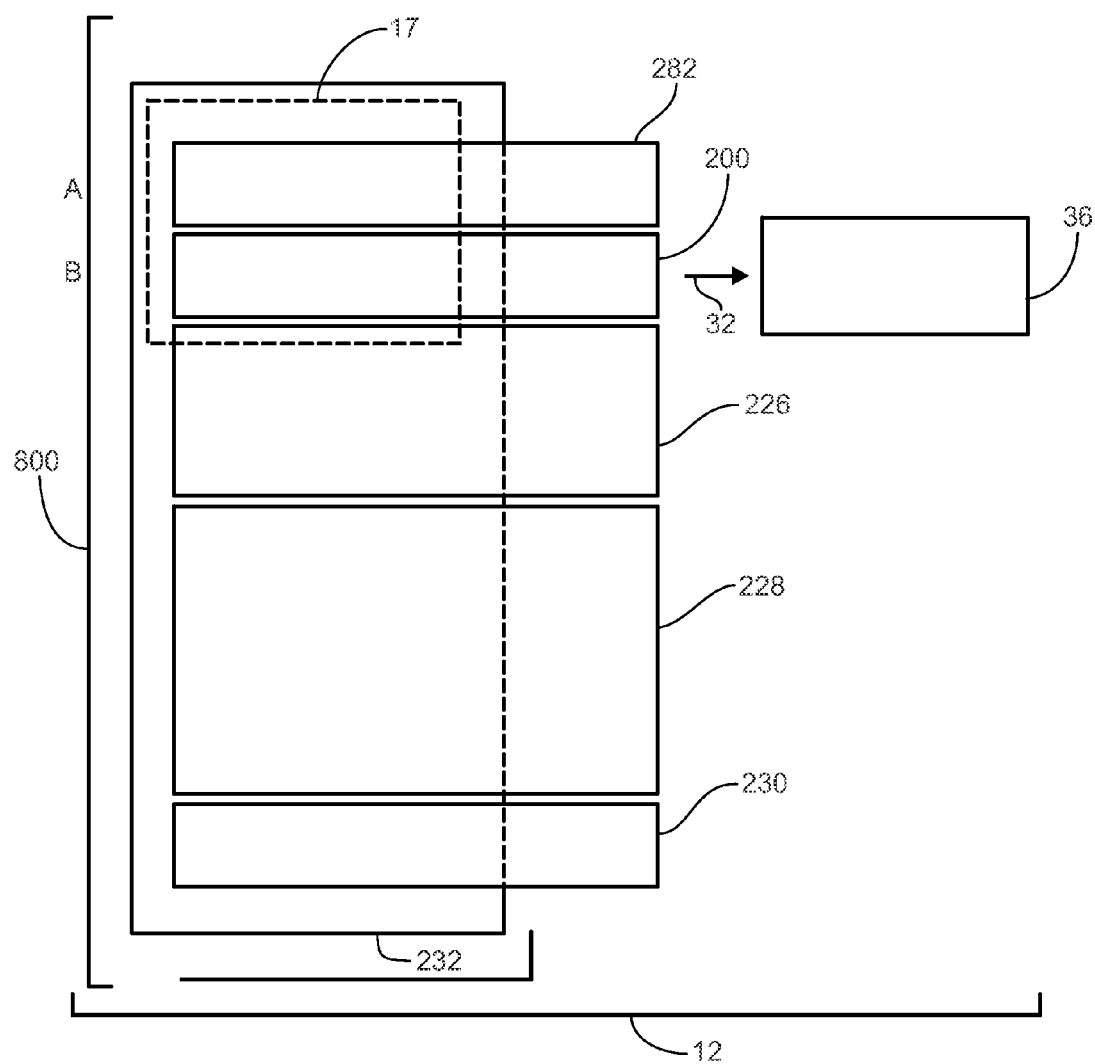
FIG. 8 is a schematic top view of an example of a flash luminescence cartridge system according to some embodiments.

Referring now to FIG. 8, another embodiment of the invention, a flash luminescence cartridge system 800, for use in an apparatus 12 for analyzing a target in a sample (not shown) is provided. Measurement of flash type luminescence requires the injection of a starter reagent (or flash luminescence reagent), and measurement of luminescence light at a fraction of a second later. The configuration of the cartridge system 800 for this application may include an injector cartridge 282, as described with respect to FIG. 7 and a luminescence cartridge 200 as described with respect to FIG. 2. The injector cartridge 282 and the luminescence cartridge 200 are positioned on adjacent slots on the cartridge support 232 as described with respect to FIG. 4. Any combination of cartridges may be possible (including multipurpose cartridges as described, for example, in above-referenced U.S. Pat. No. 8,119,066). However, the cartridges are typically dedicated to a single (or only few) applications, unless the required performance would not be compromised by including an additional application. In some embodiments, due to the proximity of the injection position and the read position, the luminescence cartridge 200 and the injector cartridge 282 are fused into a single, dual slot cartridge.

As shown in FIG. 8, the luminescence cartridge 200 is aligned with the detector 36 and detects emitting light 32 from a first target 14*a* (not shown) on the sample support 17, which is positioned below the cartridge support 232. A flash type luminescence measurement is performed by first aligning the luminescence cartridge 200 with the detector 36 in the analysis position indicated in FIG. 8. The cartridge support 232 is then in a fixed position until the sample analysis is complete. The sample support 17 is then moved to align the first sample 16*a* (not shown) with the injector cartridge 282 in a first position, i.e., an "injecting position," position A. Starter reagent is then injected onto the first sample 16*a*. After the starter reagent is injected, the sample support 17 is then moved such that the first sample 16*a* on the sample support 17 is in a second position i.e., a "reading position," position B, where the first sample 16*a* is aligned with the luminescence read head (not shown) within the luminescence cartridge 200. A measurement may be taken on a second sample 16*b* (not shown) by moving the sample support 17 to the injecting position, i.e., the "injecting position," position A, below the injector cartridge 282 and injecting starter reagent onto the second sample 16*b*. The sample support 17 is then moved such that the second sample 16*b* on the sample support 17 is in the second position i.e., the "reading position," position B, where the second sample 16*b* is aligned with the luminescence read head (not shown) within the luminescence cartridge 200.

According to another embodiment, the luminescence cartridge 300 described above and illustrated in FIG. 3 is utilized in the flash luminescence cartridge system 800, in place of the luminescence cartridge 200. In some embodiments, the luminescence cartridge 300 and the injector cartridge 282 may be integrated together as a single, dual slot cartridge. The flash luminescence cartridge system 800 may be operated with the luminescence cartridge 300 in generally the same manner as described above and illustrated in FIG. 8 in connection with the luminescence cartridge 200. However, as the luminescence cartridge 300 includes an integrated luminescence detector 308 (FIG. 3) instead of a separate read head 202 and external output detector 36 (FIG. 2), the luminescence cartridge 300 does not need to be aligned with the output detector 36. For each sample 16 being interrogated, the sample carrier 54 is simply moved to the injection position A to align the sample 16 with the injector cartridge 282 and inject the starter reagent, and then moved to the reading position B to align the sample 16 with the luminescence detector 308 and take the luminescence measurements for that particular sample 16.

Figure 9A:
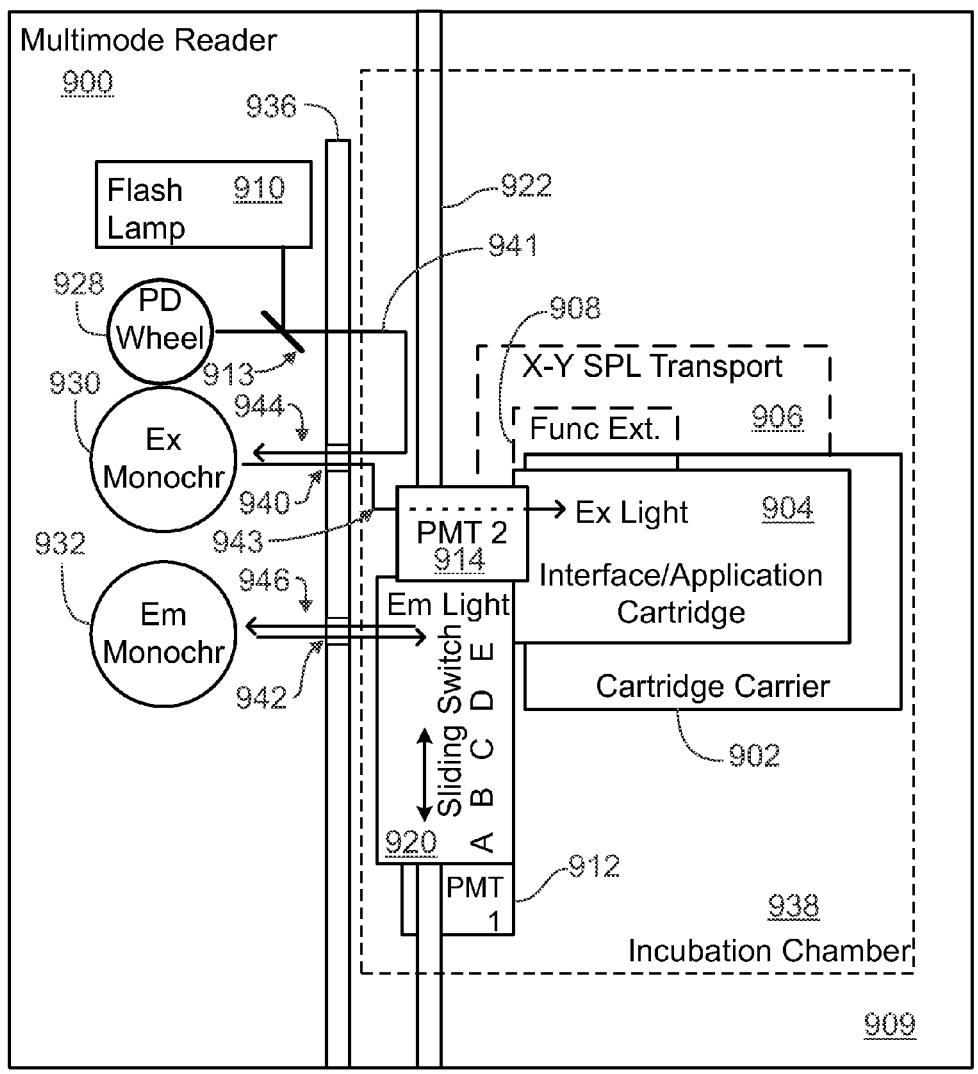
FIG. 9A is a schematic top view of an example of a sample analyzing system or apparatus according to some embodiments.
Figure 9B:
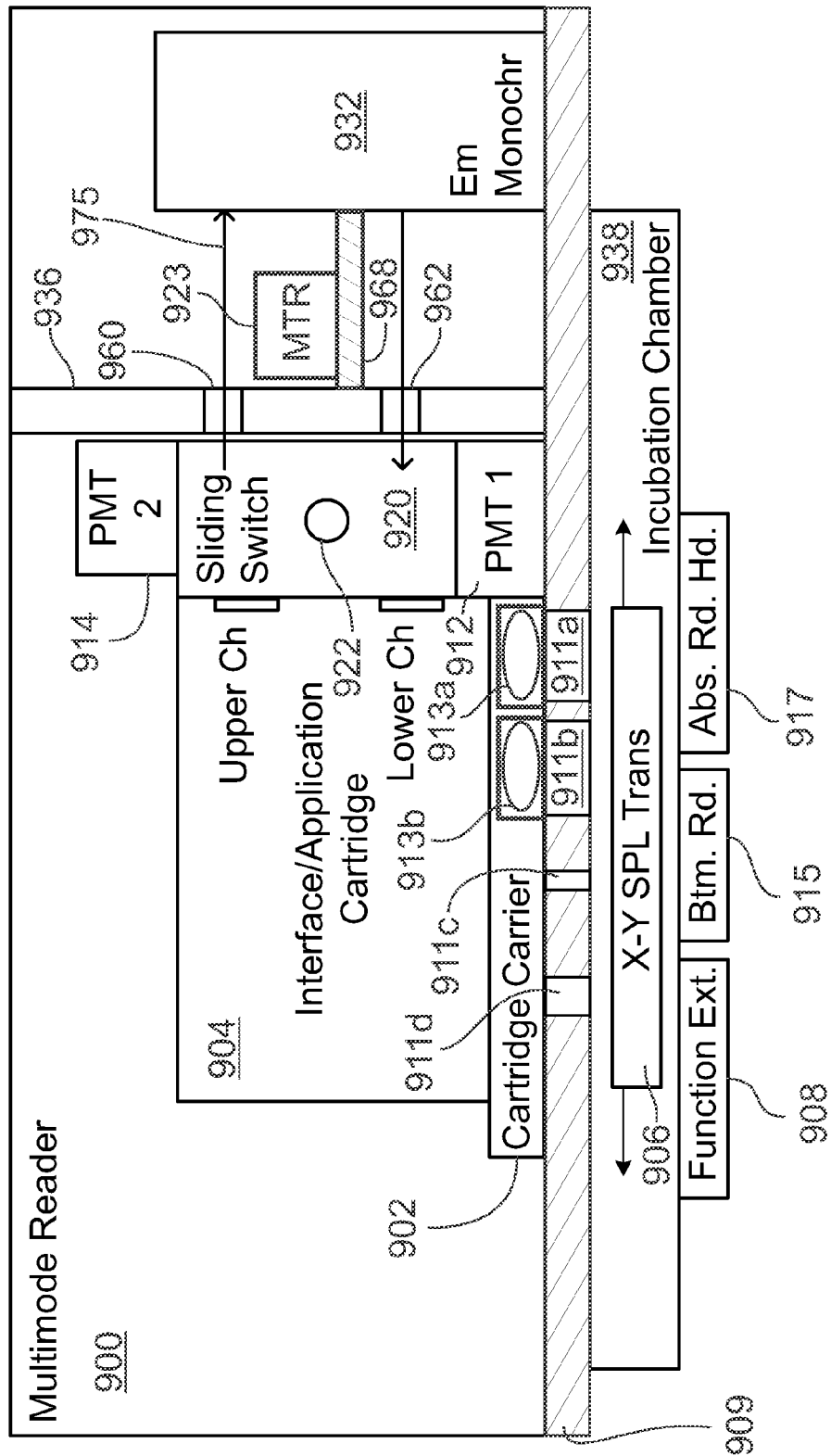
FIG. 9B is a schematic side view of the sample analyzing system or apparatus illustrated in FIG. 9A.

FIGS. 9A and 9B are schematic top side views, respectively, of another example of a sample analyzing system or apparatus 900 according to some embodiments. FIG. 9B is a schematic side view of the sample analyzing apparatus 900 illustrated in FIG. 9A. The sample analyzing apparatus 900 includes a cartridge carrier 902 configured to support one or more application cartridges (and/or interface cartridges) 904. The cartridge carrier 902 and application cartridges 904 may be designed to provide support for existing applications and technologies, such as for example, applications and cartridges provided by the SpectraMax® Paradigm™ and SpectraMax® i3™ systems available from Molecular Devices, LLC, Sunnyvale, Calif., USA. The application cartridges 904 may also be future cartridges configured to operate with a common form factor dictated by an interface cartridge that may operate as an application cartridge as described below.

The sample analyzing apparatus 900 also includes a sample support 906, which is shown in FIGS. 9A and 9B as being positioned underneath a bottom plate 909 of the sample analyzing apparatus 900 and inside an incubation chamber 938. The sample support 906 may be implemented as a carrier for multiple samples removably mounted on an x-y transport. The samples may be placed in sample holders or wells arranged on a planar tray structure. In the example implementations described herein, the multiple sample holder is implemented using a microplate, which is known in the art as a sample holder typically used in detection systems. The reference herein to a microplate is not however intended as limiting. Those of ordinary skill in the art would understand that other suitable sample holders may be used as well. It is to be understood that the sample support 906 refers to the microplate and x-y transport as a unit in this description.

The sample analyzing apparatus 900 includes a light source implemented using a flash lamp module 910, and an LED wheel 928. The flash lamp module 910 or an LED on the LED wheel 928 generates an excitation light along an excitation light path 941, which is directed through the system using directing optics devices strategically placed in the system housing. Directing and selecting optics, such as an excitation light splitter 913, may be controlled to guide a selected excitation light from either the flash lamp module 910 or the LED wheel 928. The flash lamp module 910 may be any suitable flash lamp, such as a Xenon flash lamp, and an interface for controlling on/off state, duty cycle, and any other parameters that may be advantageously controlled for the applications performed by the system 900. The LED wheel 928 includes a plurality of high-powered LEDs positioned on the periphery of the LED wheel 928, which may be rotated using a motor to insert the selected LED in the excitation light path 941.

The detection devices are implemented in the sample analyzing apparatus 900 using an absorbance detector (such as a photodiode, for example) mounted on an absorbance reader module 917 in FIG. 9B, a first PMT 912, and a second PMT 914. The absorbance read head 917, a bottom fluorescence optics module 915, and a function expander module 908 may be mounted under the bottom plate 909 of the housing. In addition, as shown in FIG. 9B, the absorbance reader module 917, the bottom fluorescence optics module 915, and the function expander module 908 are mounted under the incubation chamber 938, which holds the sample support 906.

The bottom plate 909 may include four openings. A first opening 911a provides access for an excitation light along an excitation optical path aligned with an absorbance lens assembly 913a and a sample on the sample carrier to perform absorbance measurements. A second opening 911b in the bottom plate 909 provides access for optical paths formed for top-side fluorescence and luminescence measurements and aligned with a top fluorescence/luminescence lens assembly 913b. A third opening 911c in the bottom plate 909 may be used to insert a light guide into the incubation chamber 938 in close proximity to a selected sample in the sample carrier that may be used to receive luminescence emission light in accordance with specific applications. A fourth opening 911d in the bottom plate 909 may be used for access by components in the function expander module 908. In an example implementation, the function expander module 908 may be an imaging system interface that permits a cell imaging system under the multimode reader 900 to use resources available on a cartridge, such as illuminating functions or fluid injection functions as described below.

The first PMT 912 may be a standard photomultiplier tube that may be used in most applications performed by the sample analyzing apparatus 900. The second PMT 914 may be a specialized photomultiplier tube such as for example a UV/VIS (for measuring ultraviolet as well as visible light) or a UV/VIS/NIR (for measuring ultraviolet or near infrared as well as visible light). The second PMT 914 may be designated as optional in example implementations such that it is installed per customer specification.

The sample analyzing apparatus 900 includes an excitation monochromator 930 and an emission monochromator 932 configured to receive a light and to transmit the light at a selected wavelength. The sample analyzing apparatus 900 also includes an optical configuration panel 936 that may be used to configure the direction and characteristics of the optical paths between light source and detectors, and to control light transmission into and out of the excitation monochromator 930 and emission monochromator 932. The optical configuration panel 936 may include a first set of optical ports 940 for directing the excitation light path 941 to and from the excitation monochromator 930 and a second set of optical ports 942 for directing an emission light path to and from the emission monochromator 932.

The excitation monochromator 930 may be controlled to spread the received excitation light into its component wavelengths and to output a selected one of the wavelengths along the excitation light path 941. Particular applications may operate with an excitation light at a particular wavelength. The excitation monochromator 930 may receive the generally white light generated by the flash lamp module 910 and outputs the excitation light at the wavelength selected for the application.

The excitation monochromator 930 and the emission monochromator 932 may be implemented as double stacked gratings configured as a subtracting double monochromator. The excitation monochromator 930 and the emission monochromator 932 may be enclosed in a substantially wall-off chamber that may include a middle plate 168 between the top and bottom gratings of each monochromator.

Particular applications may also require measurement of an emitted light from a sample at a selected wavelength. The emitted light from the sample may be directed to the second set of optical ports 942. An input emission light 946 is directed from the second set of ports 942 to the emission monochromator 932. The emission monochromator 932 directs the selected wavelength component of the emission light 942 to the second set of ports 942 towards optics that directs the emission light towards a selected detector.

In the example implementation described here with reference to FIGS. 9A and 9B, the excitation monochromator 930 and emission monochromator 932 may be implemented as top and bottom level monochromators. For example, in FIG. 9B, the emission monochromator 932 includes a top level that receives the emission light 946 at an emission monochromator entrance slit 960 on the optical configuration panel 936. The top level of the emission monochromator 932 includes a top grating, which spreads the emission light on the emission light path 946 into multiple light paths each at the component wavelengths of the emission light. A mirror on the optical configuration panel 936 is positioned at an angle for receiving the selected wavelength component of the emission light. The selected wavelength component of the emission light is directed to another mirror on the optics configuration pane, which directs the emission light to the lower level grating of the emission monochromator 932. The emission light is again spread into its component wavelengths, which may be limited substantially to the wavelength selected for the top level of the emission monochromator 932. The lower level of the emission monochromator 932 is positioned to place the selected wavelength component of the emission light at an emission monochromator exit slit 962.

The emission monochromator entrance slit 960 and emission monochromator exit slit 962 accommodate the two-level grating structure of the emission monochromator 932. The dual-level optical path options available using the emission monochromator entrance slit 960 and emission monochromator exit slit 962 may also accommodate a dual-channel optical path format of the cartridges used as application and/or interface cartridges 904.

Application cartridges may be used to perform measurements according to existing applications available prior to an implementation of the sample analyzing apparatus 900, or after to conform to the sample analyzing apparatus 900. An interface cartridge may be used to perform measurements using a variety of detection modes. Accordingly, the term "interface cartridge 904" is used in place of the term "application and/or interface cartridge 904" except where the context warrants the use of the term "application and/or interface cartridge 904."

The interface cartridge 904 includes optical components arranged to provide multiple paths for excitation and emission light paths that are selectable according to specific applications, or more specifically, specific detection modes. For example, the interface cartridge 904 may be moved to a position that guides the excitation light path 944 exiting the excitation monochromator 930 to the sample on the sample support 906 for an absorbance measurement. The interface cartridge 904 may also include an optics path that guides the excitation light path 944 through fluorescence measurement optics, which directs the excitation light to the sample and the emission light generated by the sample to one of the detectors.

The interface cartridge 904 may be used in conjunction with a sliding switch mechanism 920 to configure optics paths between light source and detectors for applications that involve using monochromators, the flash lamp module 910, the LED wheel 928 and any of the detectors (photodiode and PMTs). The interface cartridge 904 and the sliding switch mechanism 920 are movable to enable positioning the interface cartridge 904 and the sliding switch mechanism 920 in position to provide a desired light path. The interface cartridge 904 may be moved by positioning the cartridge carrier 902, and the sliding switch mechanism 920 may be moved by a motor in conjunction with a sliding switch guide rail 922.

As one non-limiting example of a configuration, FIG. 1A illustrates that the sliding switch mechanism 920 is selectively movable to five different positions A, B, C, D, and E. At position A, the sliding switch mechanism 920 blocks light to the PMTs 912 and/or 914 when not being utilized for detection. At position B, emission light received from a bottom fluorescence measurement via suitable optics (e.g., an emission fiber) is directed to the first PMT 912. At position C, an upper cartridge light path is directed to the first PMT 912 without utilizing the emission monochromator 932. At position D, one or more light paths may be formed: a top interface cartridge light path may be directed to the second PMT 914; a lower application (non-interface) cartridge light path may be directed to the first PMT 912; top and lower application (non-interface) cartridge light paths may be directed to the second PMT 914 and the first PMT 912, respectively; and a top application (non-interface) cartridge light path may be directed to the second PMT 914. As further examples in the case of luminescence measurement, position C may be utilized to direct luminescence light emitted from a sample to the first PMT 912, and position D may be utilized to direct luminescence light emitted from a sample to the second PMT 914.

Referring to FIG. 9B, the bottom fluorescence optics module 915 includes a bottom fluorescence read head positioned below the sample support 906, which in turn is positioned below the bottom plate 909. By this configuration, the bottom fluorescence read head may be utilized to direct excitation light to the sample from below the sample support 906, and/or receive fluorescence light emitted from the sample from below the sample support 906. Suitable optics, such as an excitation fiber and emission fiber extending from the optics configuration panel 936, may be coupled to the bottom fluorescence optics module 915 to route excitation light to the bottom fluorescence read head from an appropriate light source, and to route emission light from the bottom fluorescence read head to an appropriate detector.

Additional details regarding various embodiments consistent with the sample analyzing apparatus 900 described above in conjunction with FIGS. 9A and 9B are described in above-referenced U. S. Patent Application Pub. No. 2014/0191138.

Figure 10:
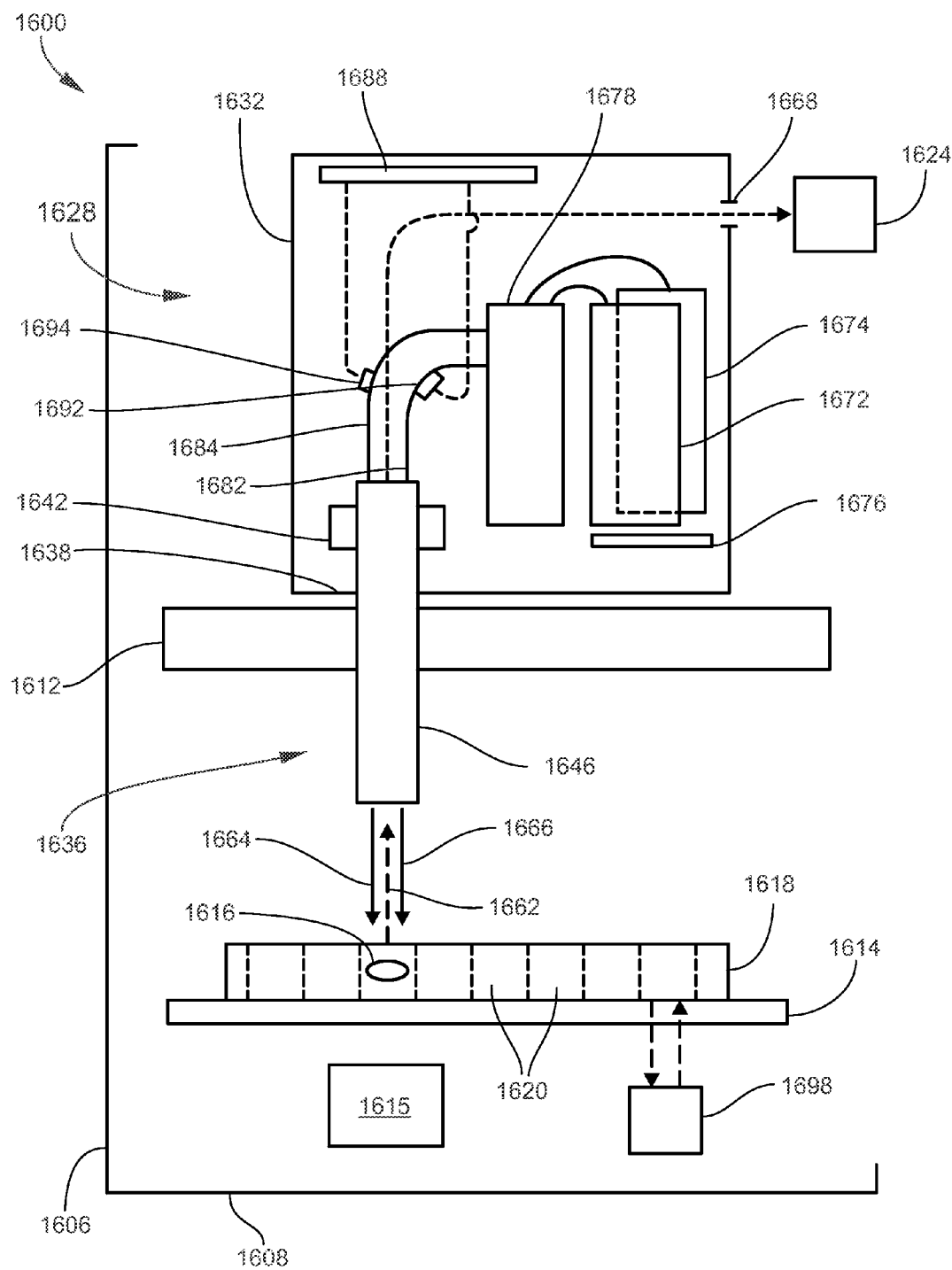
FIG. 10 is a schematic view of an example of a sample analyzing system or apparatus according to some embodiments.

FIG. 10 is a schematic view of another example of a sample analyzing system or apparatus 1600 according to some embodiments. The sample analyzing apparatus 1600 may generally include an apparatus housing enclosing various components of the sample analyzing apparatus 1600. FIG. 10 illustrates a front wall 1606 (or portion thereof) and a bottom wall 1608 (or portion thereof) of the apparatus housing. The sample analyzing apparatus 1600 may also generally include a movable cartridge support 1612 configured for supporting one or more cartridges, and a movable sample carrier 1614 for supporting one or more samples 1616 under investigation or for supporting a sample support 1618 that holds or contains such samples 1616. For example, the sample support 1618 may be an optical plate providing a plurality of wells 1620 containing individual samples 1616. The cartridge support 1612 may be movable between an inside cartridge support position (as illustrated) at which the cartridge support 1612 is positioned entirely in the apparatus housing, and an outside cartridge support position at which the cartridge support 1612 is positioned at least partially outside the apparatus housing to facilitate loading of one or more cartridges thereon. Similarly, the sample carrier 1614 may be movable between an inside sample carrier position (as illustrated) at which the sample carrier 1614 is positioned entirely in the apparatus housing, and an outside sample carrier position at which the sample carrier 1614 is positioned at least partially outside the apparatus housing to facilitate loading of one or more samples 1616 (or a sample support 1618 holding one or more samples 1616) thereon. The sample analyzing apparatus 1600 may also generally include one or more optical detectors 1624 configured for collecting optical detection signals from one or more different types of cartridges operatively loaded on the cartridge support 1612. Generally, the structure and operation of any or all of the foregoing components of the sample analyzing apparatus 1600 may be consistent with those described above in conjunction with other embodiments disclosed herein.

FIG. 10 also illustrates an example of a luminescence cartridge 1628 according to some embodiments. Like other cartridges described above, the luminescence cartridge 1628 is sized and configured to be removably loaded (i.e., mounted or installed) on the cartridge support 1612, and may be replaced or exchanged with other cartridges of the same or different type as desired. The luminescence cartridge 1628 includes a cartridge housing 1632 and an injector assembly 1636 at least partially disposed in the cartridge housing 1632 and movable through an opening 1638 of the cartridge housing 1632. In typical embodiments, the injector assembly 1636 is linearly movable in a reciprocating manner, the injector assembly 1636 may be alternately extended and retracted. Hence, the injector assembly 1636 is movable alternately toward and away from the cartridge housing 1632, and thus alternately toward and away from the sample carrier 1614 and any sample 1616 with which the injector assembly 1636 is operatively aligned. Depending on the design and location of the cartridge support 1612, the cartridge support 1612 may also include an opening to accommodate the movement of the injector assembly 1636.

To actuate and control the movement of the injector assembly 1636, the luminescence cartridge 1628 includes a driver 1642 (or drive mechanism, or drive assembly) that is coupled to the injector assembly 1636. The driver 1642 may be mounted at the cartridge housing 1632 in any suitable manner, and in typical embodiments is contained within the interior of the cartridge housing 1632. As appreciated by persons skilled in the art, the driver 1642 may have any configuration suitable for moving (i.e., retracting and extending) the injector assembly 1636 to any selected position relative to the cartridge housing 1632 (and thus relative to the sample carrier 1614 and any selected sample 1616 supported thereon). In a typical embodiment, the driver 1642 includes a motor (e.g., a micromotor) coupled to a linkage or transmission that is in turn coupled to the injector assembly 1636. The driver 1642 may include bearings or other appropriate components necessary for facilitating reliable and accurate actuation of the injector assembly 1636. The linkage or transmission may have any configuration suitable for converting the rotational movement of the motor to linear movement of the injector assembly 1636. For example, the linkage or transmission may include a set of gears such as a rack and pinion, a set of bevel gears, a worm and worm gear, etc.

To facilitate loading of luminescence cartridge 1628 on the cartridge support 1612 and subsequent removal therefrom, and to prevent damage to the injector assembly 1636 during loading and removal, the injector assembly 1636 may be fully retractable within the cartridge housing 1632 by the driver 1642 such that no part of the injector assembly 1636 extends outside of the cartridge housing 1632. The injector assembly 1636 may also be moved to the fully retracted position while the cartridge support 1612 is moving the injector assembly 1636 (and any other cartridges loaded on the cartridge support 1612) to different positions within the apparatus housing. However, the injector assembly 1636 typically does not need to be moved when acquiring luminescence data from multiple samples. That is, as noted elsewhere multiple samples may be provided at individual sites of a sample support 1618, such as in different wells 1620 of a multi-well plate that is supported on the sample carrier 1614. The injector assembly 1636 may be moved to a desired distance from the first sample 1616 which, in the illustrated "top reading" example, is a desired elevation above the first sample 1616. This desired distance will typically be the same for all samples contained on the sample support 1618. Thus, the position of the injector assembly 1636 typically does not need to be adjusted as the sample carrier 1614 moves the sample support 1618 to sequentially align one sample after another with the injector assembly 1636 to take sequential luminescence readings.

In some embodiments, the sample analyzing apparatus 1600 may also include a bottom read head 1615, which may be appropriately coupled to optics and operate as generally described elsewhere in the present disclosure. The bottom read head 1615 may be optically aligned with the injector assembly 1636. This configuration enables injection from top and bottom fluorescence reading at the same time.

Figure 11:
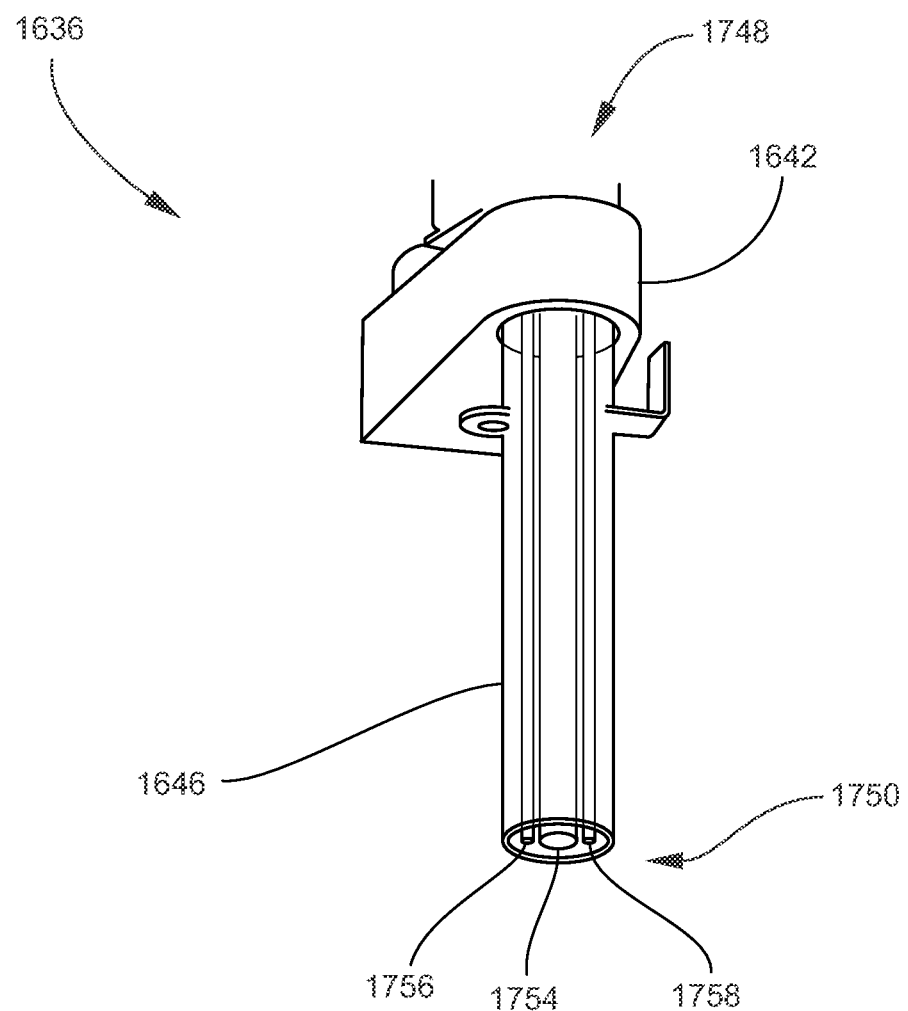
FIG. 11 is a perspective view of an example of an injector or injector/reader assembly according to some embodiments.

FIG. 11 is a perspective view of an example of the injector assembly 1636 according to some embodiments. The injector assembly 1636 includes an injector housing 1646 generally elongated between a proximal end 1748 and a distal end 1750 of the housing 1646. In typical embodiments, the injector housing 1646 is cylindrical with a circular cross-section although in other embodiments may have a polygonal cross-section. The injector assembly 1636 includes a light guide 1754 and one or more injector needles 1756 and 1758 (two in the illustrated embodiment) extending through the injector housing 1646 generally in parallel with each other. In some embodiments, the injector assembly 1636 includes a light guide 1754 extending through the injector housing 1646 generally in parallel with the injector needles 1756 and 1758. In such embodiments, the injector assembly 1636 may also be referred to as an injector/reader assembly. The light guide 1754 and injector needles 1756 and 1758 may extend all the way down to the distal end 1750 or may terminate at a small distance short of the distal end 1750. The light guide 1754 is configured for transmitting luminescent light emitted from the sample 1616 to a luminescence detector. For this purpose, the light guide 1754 may be an optical fiber, a light pipe, etc. The injector needles 1756 and 1758 are configured for dispensing fluid onto the sample 1616 (e.g., into selected wells 1620 of the sample support 1618), such as reagents as may be utilized for glow luminescence or flash luminescence as appreciated by persons skilled in the art. The integration of the light guide 1754 and the injector needles 1756 and 1758 into the single injector assembly 1636 particularly facilitates flash luminescence. Moreover, the provision of two or more injector needles 1756 and 1758 facilitates the use of different types of reagents. For example, the first injector needle 1756 may dispense a first reagent and the second injector needle 1758 may dispense a second reagent. In one specific, yet non-limiting example, the first reagent may be firefly luciferase and the second reagent may be *Renilla* luciferase. Hence, the distal end 1750 of the injector assembly 1636 may serve both as an optical input and a fluid output of the injector assembly 1636.

Referring back to FIG. 10, luminescent light directed into the injector assembly 1636 from the sample 1616 is depicted by a dashed arrow 1662, and fluid streams directed out from the injector assembly 1636 from the first injector needle 1756 and second injector needle 1758 are depicted by solid arrows 1664 and 1666, respectively. As also shown in FIG. 10, the cartridge housing 1632 may include an optical port 1668 aligned with the luminescence detector 1624 for enabling the luminescent light to be transmitted to the luminescence detector 1624. The dashed line leading from the injector assembly 1636 to the luminescence detector 1624 may represent light guide 1754 (FIG. 11) extending out from the proximal end of the injector assembly 1636 and to or through the optical port 1668. Alternatively, the light guide 1754 may terminate at some point in the cartridge housing 1632, in which case the dashed line between the injector assembly 1636 and the luminescence detector 1624 may at least partially represent one or more other types of optical components (mirrors, etc.) configured for directing the luminescent light to the luminescence detector 1624. As an alternative to utilizing the external luminescence detector 1624, the luminescence cartridge 1628 may include an internal detector (not shown) in the cartridge housing 1632 that communicates with electronics of the sample analyzing apparatus 1600 outside the luminescence cartridge 1628.

As further shown in FIG. 10, the luminescence cartridge 1628 includes one or more liquid reservoirs (e.g., bottles) such as reagent reservoirs 1672 and 1674. The reagent reservoirs 1672 and 1674 may be disposed on a reservoir support 1676, which may be movable alternately into and out from the cartridge housing 1632 as described below. The one or more reagent reservoirs 1672 and 1674 may fluidly communicate with the injector assembly 1636 via a pump 1678 (e.g., a pump assembly or pump system). The pump 1678 may represent one or more pumps (or pump units). For example, the first reagent reservoir 1672 may communicate with the first injector needle 1756 (FIG. 11) via a first fluid line 1682 (e.g., tube) to supply a first reagent, and the second reagent reservoir 1674 may communicate with the second injector needle 1758 (FIG. 11) via a second fluid line 1684 to supply a second reagent. The fluid lines 1682 and 1684, as well as the light guide 1754, should have a length and flexibility sufficient to accommodate the alternating extension and retraction of the injector assembly 1636.

Referring to FIG. 11, in some embodiments the injector assembly 1636 does not include the light guide 1754. In such embodiments luminescent light emitted from the sample 1616 may, for example, be transmitted to the bottom read head 1615 positioned below the sample 1616 (i.e., below the sample carrier 1614 and sample support 1618 shown in FIG. 10) and routed via appropriate optics (e.g., a light guide such as an optical fiber) to the luminescence detector 1624. Alternatively, luminescent light may transmitted directly to a luminescence detector (not shown) positioned below the sample 1616, without utilizing a bottom read head 1615 or other transmitting optics.

The luminescence cartridge 1628 may also include electronics 1688 configured for communicating with and/or controlling various components of the luminescence cartridge 1628. The electronics 1688 may include one or more circuits and other electrical hardware mounted on one or more support substrates such as, for example, printed circuit boards (PCBs). In addition to or as part of the electronics 1688, the luminescence cartridge 1628 may include an electrical connector configured for removable coupling to the sample analyzing apparatus 1600 (e.g., a complementary electrical connector of sample analyzing apparatus 1600) to receive power from and transmit signals to or from the sample analyzing apparatus 1600, as described above in conjunction with other embodiments such as that illustrated in FIG. 3. Thus, as described above the electrical coupling may be effected by plugs and sockets, male and female connectors, etc., whereby certain components of the luminescence cartridge 1628 are placed in signal communication with a power source or system controller of the sample analyzing apparatus 1600 as appropriate (e.g., the power source 44 and system controller 74 described above and illustrated in FIG. 3).

An example of a method for analyzing a sample 1616 will now be described with reference to FIGS. 10 and 11. The luminescence cartridge 1628 is loaded (or installed) on the cartridge support 1612 to position the luminescence cartridge 1628 in the apparatus housing of the sample analyzing apparatus 1600. Loading may include opening a panel or door such as may be located at the front wall 1606 of the apparatus housing to access the cartridge support 1612. The cartridge support 1612 may first be moved to a position at least partially outside the apparatus housing, and after the luminescence cartridge 1628 is loaded on the cartridge support 1612, the cartridge support 1612 may then be moved back into the apparatus housing with the luminescence cartridge 1628 loaded thereon. Loading may also entail coupling the luminescence cartridge 1628 with the sample analyzing apparatus 1600 via electrical connectors as described above to establish paths for transmitting power, data and control signals. Before or after loading the luminescence cartridge 1628, the sample 1616 is loaded on the sample carrier 1614, typically by first loading the sample 1616 on a sample support 1618 and in turn loading the sample support 1618 on the sample carrier 1614. A plurality of samples 1616 may be loaded together on an appropriate sample support 1618 such as a multi-well plate. Ultimately, the cartridge support 1612 and the sample support 1618 will be positioned relative to each other such that the sample 1616 will be aligned with the injector assembly 1636. In the present context, "aligned" means optically aligned, i.e., positioned so as to establish an optical path sufficient for luminescence data acquisition from the sample 1616. The term "aligned" may also mean fluidly aligned, i.e., positioned so as to be able to dispense fluid onto the sample 1616.

The injector assembly 1636 is then moved toward the sample 1616 until its optical input end reaches a desired distance (reading position) from the sample 1616. The injector assembly 1636 may be moved very close to the sample 1616 to be interrogated, thus maximizing light collection from the target sample 1616 and minimizing stray light collection from adjacent samples. At the reading position, the pump 1678 is operated to establish a flow of a selected reagent from one of the reagent reservoirs 1672 or 1674 to the corresponding injector needle 1756 or 1758, whereby the selected reagent is injected by the injector needle 1756 or 1758 to the sample 1616 to induce luminescence in the sample 1616. The light guide 1754 of the injector assembly 1636 receives (collects) the resulting luminescent light 1662 emitted from the sample 1616 and transmits the luminescent light 1662 to the luminescence detector 1624 (or an internal detector provided in the cartridge housing 1632, not shown). The luminescence detector 1624 converts these optical signals into electrical signals (detector signals, or measurement signals) and transmits the electrical signals to signal processing circuitry, such as may be provided by a system controller of sample analyzing apparatus 1600, as described above in conjunction with other embodiments. In the case of multiple samples 1616, the sample carrier 1614 may be moved to sequentially align each additional sample 1616 with the light guide 1754, whereby luminescence measurements are taken from all samples 1616 sequentially.

In some embodiments, more than one reagent may be utilized for each sample 1616. For example, the pump 1678 may be establish a flow of a first reagent from the first reagent reservoir 1672 to the first injector needle 1756, after which the light guide 1754 receives the luminescent light 1662 emitted from the sample 1616 in response to injecting the first reagent. Subsequently, the pump 1678 may be establish a flow of a second reagent from the second reagent reservoir 1674 to the second injector needle 1758, after which the light guide 1754 receives the luminescent light 1662 emitted from the sample 1616 in response to injecting the second reagent. In some embodiments, the second reagent may include a quenching agent that quenches the signal resulting from the first reagent.

At the completion of making the luminescence measurements, the luminescence cartridge 1632, being a modular or removable cartridge as described throughout the present disclosure, may then be removed from the cartridge support 1612, and thereafter replaced with another luminescence cartridge 1632 or different type of removable cartridge as desired. Before moving the cartridge support 1612 through the apparatus housing as needed to remove the luminescence cartridge 1632, the injector assembly 1636 may be retracted to a position completely inside the cartridge housing 1632 to protect the injector assembly 1636 during movement.

Figure 12A:
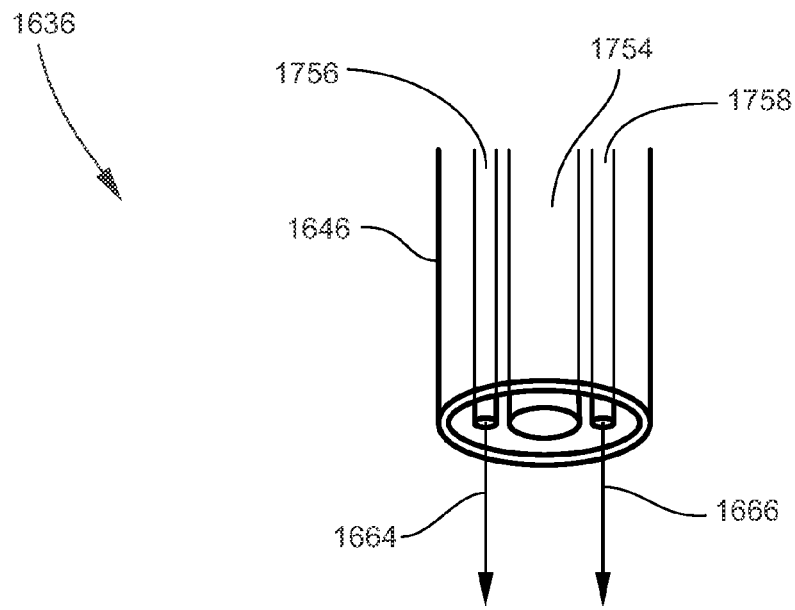
FIG. 12A is a perspective view of the tip (distal) section of the injector or injector/reader assembly illustrated in FIG. 11 when surfaces are clean and no bubbles are being generated.
Figure 12B:
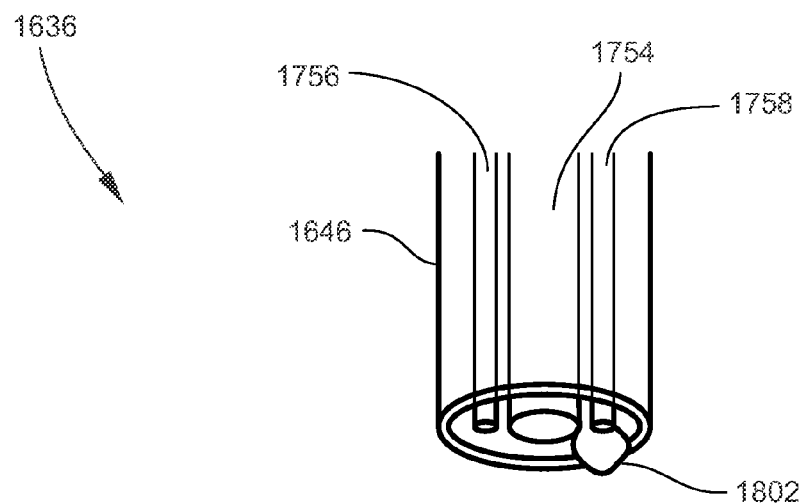
FIG. 12B is a perspective view of the tip (distal) section of the injector or injector/reader assembly illustrated in FIGS. 11 and 12A when bubbles have been generated in an associated injector system as a result of dispensing a liquid/air mixture.

The injector system of the sample analyzing apparatus 1600 (i.e., the reservoirs 1672 and 1674, pump 1678, injector needles 1756 and 1758, and associated fluid lines) need to be rinsed and possibly decontaminated after being used to clean the system between experiments as well as to prevent the clogging of fluidic components such as the pump 1678 and fluid lines. In addition, as part of preparing the injector system for use the user needs to prime the system. The rinsing and priming of the system may involve the dispensing of a mixture of liquid and air for a limited amount of time, which may generate bubbles and may also generate much larger droplets than the droplets expected for normal dispensing procedures. To illustrate this, FIG. 12A is a perspective view of the tip (distal) section of the injector assembly 1636 when surfaces are clean and no bubbles are being generated. In this case, liquid streams 1664 and 1666 are dispensed from the tips of the injector needles 1756 and 1758 in the expected way. By comparison, FIG. 12B is a perspective view of the tip (distal) section of the injector assembly 1636 when bubbles have been generated in the injector system as a result of dispensing a liquid/air mixture. In this case, liquid may accumulate (possibly as the result of surface tension holding the liquid stream back) and result in the formation of a droplet 1802 of uncontrolled size. Such a droplet 1802 will eventually separate from the injector assembly 1636, and then fall down and/or splash onto an undesired portion of the sample support 1618 (FIG. 11), or onto one or more optics components in the apparatus housing, etc. The droplet 1802 may also contaminate the input end of the light guide 1754. In all such cases, the droplet 1802 may contaminate the sample analyzing apparatus 1600 and/or cause the experiment to be aborted due to contamination.

To address this problem, in some embodiments the sample analyzing apparatus 1600 and luminescence cartridge 1628 are configured to enable rinsing and priming to be performed outside of the sample analyzing apparatus 1600. In this manner, any unavoidable dispensing of a liquid/air mixture occurs remotely from the internal optics components of the sample analyzing apparatus 1600, and all bubbles may be purged from the injector system prior to loading the luminescence cartridge 1628 into the apparatus housing of the sample analyzing apparatus 1600. The external rinsing and priming approach will now be described with reference to FIGS. 13A to 15.

Figure 13A:
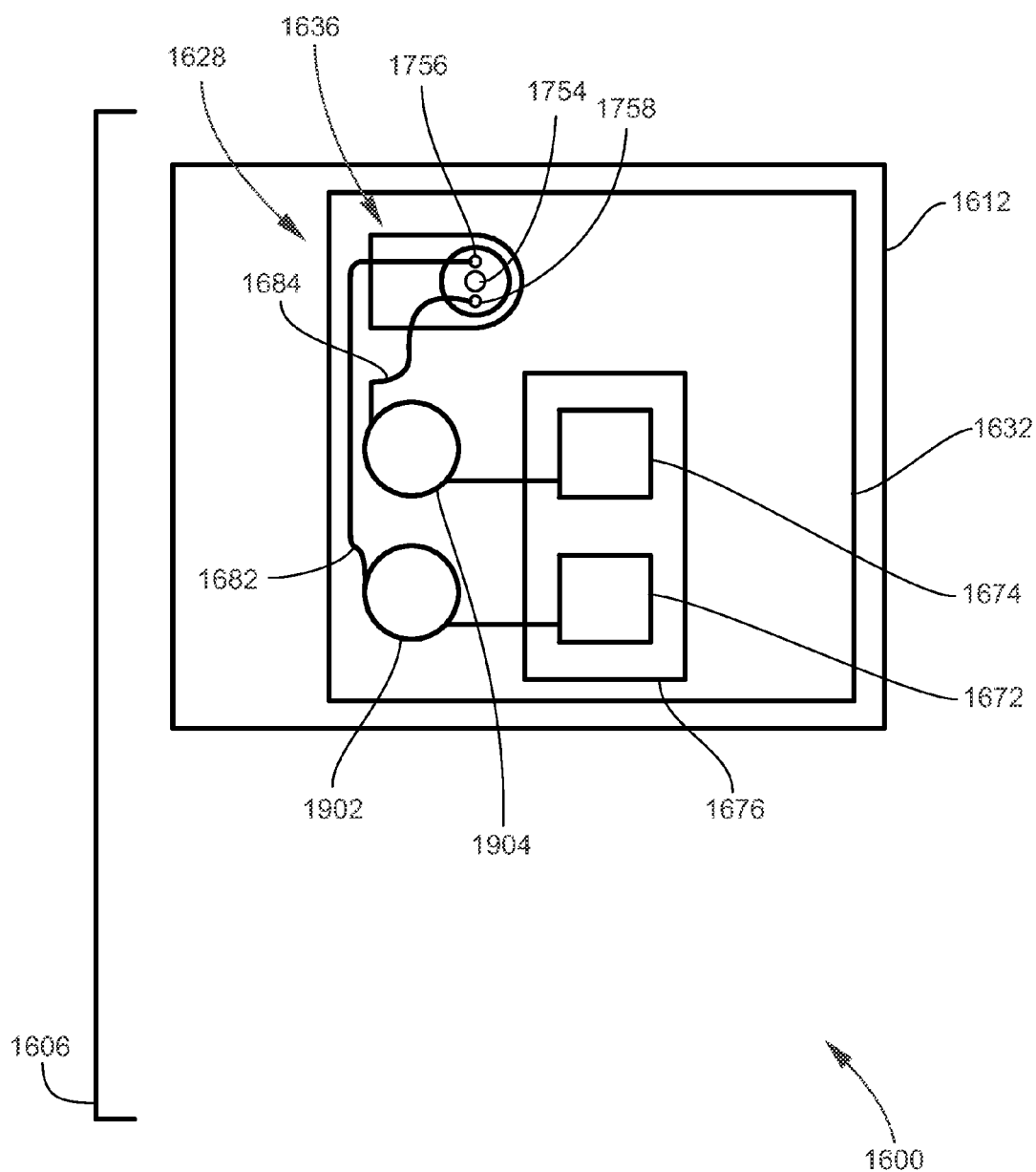
FIG. 13A is a top schematic view of the sample analyzing apparatus illustrated in FIG. 10 in which a cartridge support and a luminescence cartridge loaded thereon are in an inside position, i.e., fully inside an apparatus housing.
Figure 13B:
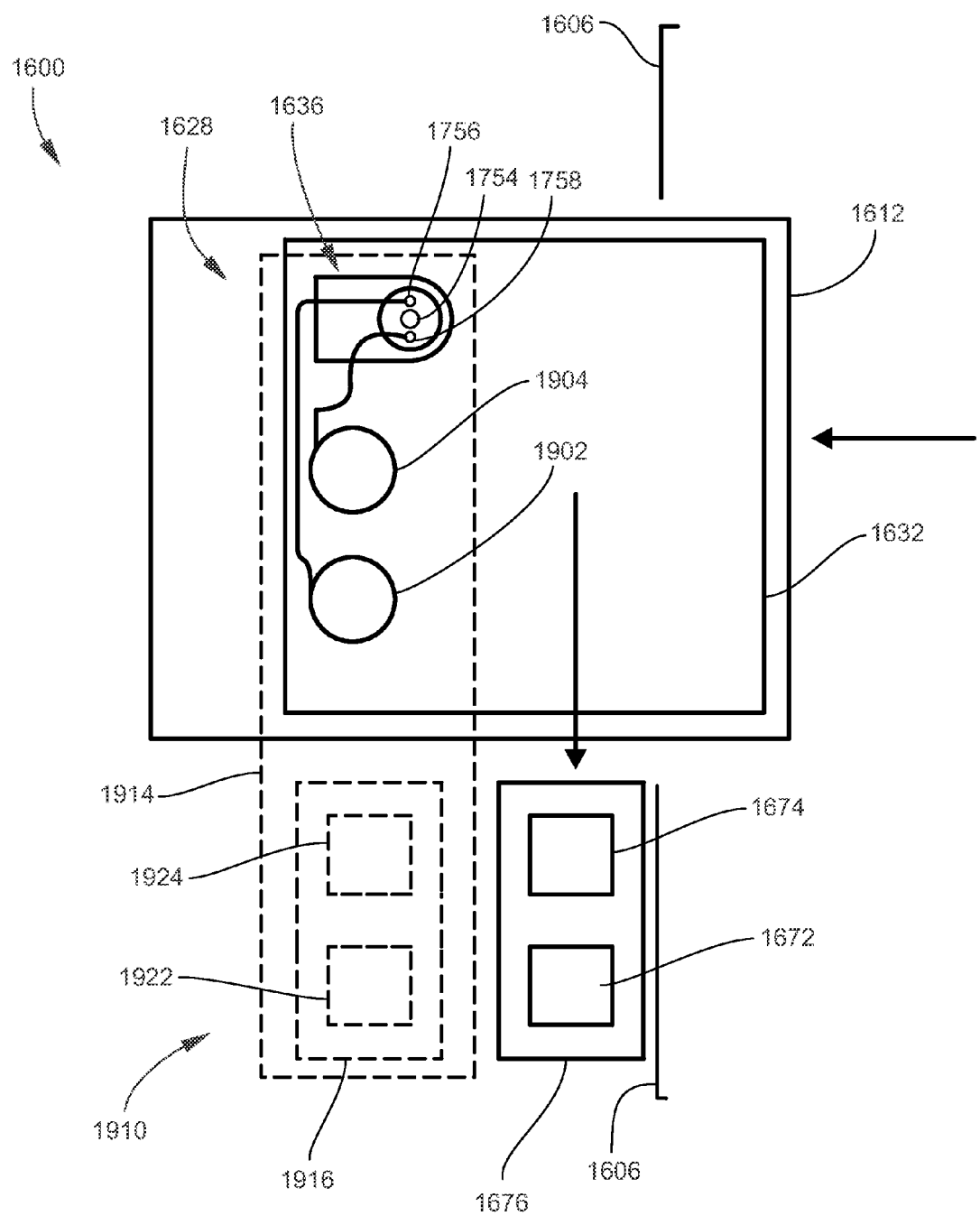
FIG. 13B is a top schematic view of the sample analyzing apparatus illustrated in FIGS. 10 and 13A in which the cartridge support and the luminescence cartridge loaded thereon are have been moved to an outside position, i.e., extending at least partially outside of the interior of the apparatus housing.

FIG. 13A is a top schematic view of the sample analyzing apparatus 1600 in which the cartridge support 1612 and the luminescence cartridge 1628 loaded thereon are in an inside position, i.e., fully inside the apparatus housing. FIG. 13A corresponds to the operative position of the luminescence cartridge 1628 at which luminescence measurements may be taken, as described above in conjunction with FIGS. 10 and 11. FIG. 13B is a top schematic view of the sample analyzing apparatus 1600 in which the cartridge support 1612 and the luminescence cartridge 1628 loaded thereon are have been moved to an outside position, i.e., extending at least partially outside of the interior of the apparatus housing. In comparison to FIG. 10, certain components of the luminescence cartridge 1628 have been rearranged for illustrative purposes. In the illustrated embodiment, the pump includes a first pump 1902 fluidly coupled between the first reservoir 1672 and the first injector needle 1756, and a second pump 1904 fluidly coupled between the second reservoir 1674 and the second injector needle 1758.

In some embodiments, to initiate a rinse and/or priming operation, the cartridge support 1612 is moved to the outside position illustrated in FIG. 13B, as depicted by the horizontal arrow. If the luminescence cartridge 1628 was already loaded on the cartridge support 1612, the luminescence cartridge 1628 is moved together with the cartridge support 1612 to the outside position. On the other hand, if the luminescence cartridge 1628 was not already loaded on the cartridge support 1612, the luminescence cartridge 1628 is loaded on the cartridge support 1612 after the cartridge support 1612 has been moved to the outside position. Once the cartridge support 1612 and luminescence cartridge 1628 are at the outside position, the reservoir support 1676 and reagent reservoirs 1672 and 1674 supported thereon may be moved to an outside position as also illustrated in FIG. 13B, by sliding the reservoir support 1676 as depicted by the vertical arrow. For this purpose, the reservoir support 1676 may be movably mounted to the cartridge housing 1632 by linear guides or tracks, etc., as appreciated by persons skilled in the art. At the outside position, the reagent reservoirs 1672 and 1674 may be replaced as needed.

Additionally, after the cartridge support 1612 and luminescence cartridge 1628 have been moved to the outside position, an external rinsing/priming station 1910 may be mounted to the cartridge support 1612 and/or luminescence cartridge 1628. The rinsing/priming station 1910 may include an external liquid container (or tank) 1914. In some embodiments, the rinsing/priming station 1910 may also include an external reservoir support 1916 for holding one or more rinsing/priming reservoirs 1922 and 1924 (e.g., bottles).

FIG. 14 is a perspective view of an example of the external rinsing/priming station 1910 according to some embodiments. FIG. 15 is a perspective view of the external rinsing/priming station 1910 as mounted to the cartridge support 1612 and/or luminescence cartridge 1628. The rinsing/priming station 1910 may include one or more mounting features as needed for mounting the rinsing/priming station 1910 to the cartridge support 1612 and/or luminescence cartridge 1628. For example, the rinsing/priming station 1910 may include a mounting feature 2028 configured for engaging the cartridge housing 1632. In the illustrated embodiment, the rinsing/priming station 1910 is configured such that the external liquid container 1914 extends below the cartridge support 1612 when in the mounting position. The external liquid container 1914 includes a port 2032 that is aligned with the injector assembly 1636 when in the mounting position. Thus, after mounting the rinsing/priming station 1910, the injector assembly 1636 may be lowered into or through the port 2032 such that the injector assembly 1636 fluidly communicates with the interior of the external liquid container 1914.

A rinsing operation may be implemented while the luminescence cartridge 1628 is in the mounting position and the injector assembly 1636 is inserted in the port 2032. First, the reagent reservoirs 1672 and 1674 may be filled with an appropriate rinse solution. Alternatively, the fluid lines from the pumps 1902 and 1904 may be disconnected from the reagent reservoirs 1672 and 1674 and reconnected to one or more rinsing reservoirs 1922 and 1924 provided at the external reservoir support 1916. Alternatively, the rinsing reservoirs 1922 and 1924 may be placed in the position of the reagent reservoirs 1672 and 1674 in preparation for rinsing, instead of utilizing (or providing) the external reservoir support 1916. In all such cases, the pumps 1902 and 1904 may then be operated to flow the rinse solution through the pumps 1902 and 1904, injector needles 1756 and 1758, and associated fluid lines, and into the external liquid container 1914 via the port 2032.

Likewise, a priming operation may be implemented while the luminescence cartridge 1628 is in the mounting position and the injector assembly 1636 is inserted in the port 2032. First, the reagent reservoirs 1672 and 1674 may be filled with the respective first reagents and second reagents. The pumps 1902 and 1904 may then be operated to flow the respective first reagents and second reagents through the pumps 1902 and 1904, injector needles 1756 and 1758, and associated fluid lines, with the excess reagent solution captured in the external liquid container 1914 via the port 2032.

Referring back to FIG. 10, apart from the rinsing and priming of the system, a liquid/air mixture may be dispensed during the normal dispensing operation of the luminescence cartridge 1628, e.g., during the dispensing of reagent or other fluid from one of the injector needles 1756 and 1758 onto the sample 1616. If the injector system is running out of liquid, it may dispense a liquid/air mixture and consequently generate bubbles. In some embodiments, this problem may be addressed by providing capacitive bubble sensors 1692 and 1694 operatively communicating with the fluid lines 1682 and 1684, respectively, between the pump 1678 and the injector needles 1756 and 1758. As depicted by dashed lines, the capacitive bubble sensors 1692 and 1694 may communicate with the electronics 1688 of the luminescence cartridge 1628.

Figure 16:
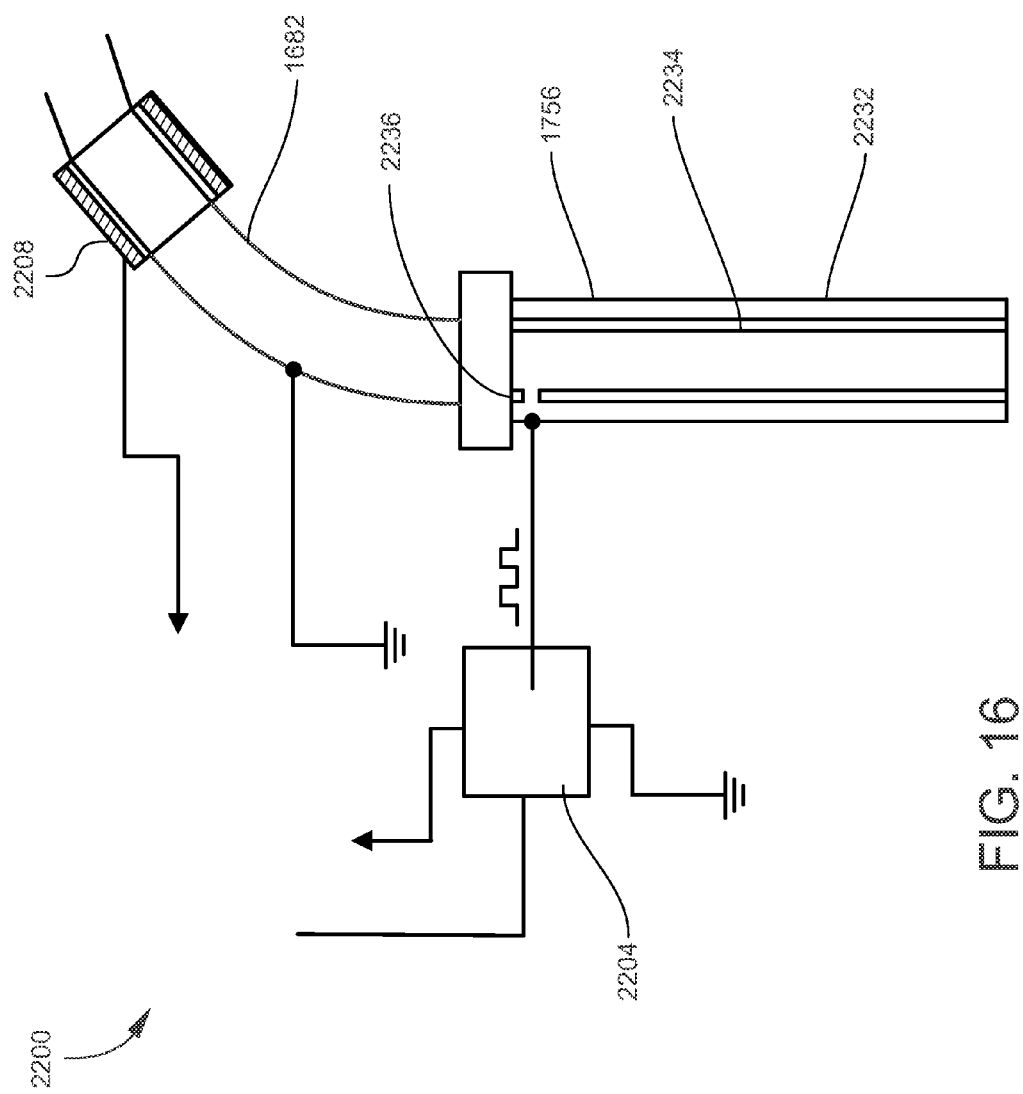
FIG. 16 is a schematic view of an example of a capacitive bubble sensor in operative communication with an injector needle and associated fluid line (shown in cross-section) according to some embodiments.

FIG. 16 is a schematic view of an example of a capacitive bubble sensor 2200 in operative communication with one of the injector needles 1756 and associated fluid line 1682 (shown in cross-section) according to some embodiments. The capacitive bubble sensor 2200 may include a signal generator 2204 electrically communicating with the injector needle 1756, such as by tapping an electrical lead from the signal generator 2204 to an electrically conductive portion of the injector needle 1756 that is exposed to the fluid flow.

The capacitive bubble sensor 2200 may also include a detector 2208 (e.g., a metal sleeve, or a metal tubing connector that connects two tubes, etc.) that at least partially surrounds a portion of the fluid line 1682. By this configuration, the electrically conductive portion of the injector needle 1756 (contacting the electrolytic fluid flowing through the injector needle 1756) forms one side of the capacitor, the detector 2208 forms the other side of the capacitor, and the wall of the fluid line 1682 serves as the dielectric between the two sides of the capacitor. Electrical leads connect the signal generator 2204 and the detector 2208 to the electronics 1688 (FIG. 10) of the luminescence cartridge 1628. An additional electrical lead from the electronics 1688 may provide a source of voltage to the signal generator 2204. In operation, the signal generator 2204 may transmit a pulse to the injector needle 1756, such as between ground and a low voltage value (e.g., 2 V). The electronics 1688 are configured to continuously measure the capacitance between the two sides of the capacitor formed by the foregoing arrangement, and to detect when a change in capacitance correlates to the presence of a bubble, as appreciated by persons skilled in the art. The electronics 1688 may be configured to shut down the liquid dispensing operation when a bubble is detected, thereby preventing contamination of the internal optics of the sample analyzing apparatus 1600 (FIG. 10). For example, the electronics 1688 may transmit an output (control) signal to the pump 1678 (FIG. 10), or to a pump controller controlling the pump 1678, that ceases operation of the pump 1678.

Another problem that may arise during the course of operating the injector system is the generation of unwanted microdroplets that may also contaminate the optics of the sample analyzing apparatus 1600. Such microdroplets may be accelerated by electrostatic forces developed in dielectric materials utilized in the sample analyzing apparatus 1600. Such dielectric materials may include, for example, the sample support 1618, certain pump components contacting the liquid, and one or more portions of the injector needles 1756 and 1758 (e.g., lining, coated tip, etc.). This problem may be addressed by grounding dielectric components where practicable to minimize or eliminate electrostatic forces.

For example, in the embodiment illustrated in FIG. 16, the injector needle 1756 may include an electrically conductive (e.g., metal) wall 2232, the inside surface of which is lined with a non-metal (and dielectric) coating (or layer) 2234 such as polytetrafluoroethylene (PTFE) to render the inside surface inert to the liquid. The electrically conductive wall 2232 may be placed in communication with an electrical ground. In embodiments providing the capacitive bubble sensor 2200, the electrical connection between the electrically conductive wall 2232 and the signal generator 2204 (which is grounded) may be utilized for this purpose. At this electrical connection, a portion of the non-metal coating 2234 may be removed (may be absent) to expose the liquid to the electrically conductive wall 2232 at this location. That is, the non-metal coating 2234 may include an uncovered region 2236 not covered by the non-metal coating at this location.

Alternatively, in another embodiment the coating 2234 may have a non-metal composition that renders the coating 2234 electrically conductive instead of exhibiting dielectric behavior. For example, the composition of the coating 2234 may be an organic polymer having sufficient carbon to be electrically conductive, such as a conductive polymer or a normally dielectric formulation such as PTFE that is modified to have a higher carbon content. In such embodiments, either the wall 2232 or the coating 2234 may be grounded.

As another alternative, at least a portion of the injector needle 1756 or a coating 2234 thereon may be composed of an antistatic plastic, which may be placed in communication with an electrical ground.

In addition to or as an alternative to one or more of the foregoing embodiments, the fluid line 1682 may be connected to electrical ground as illustrated. Additionally, the fluid line 1682 may be composed of or coated with an antistatic plastic.

Referring back to FIG. 10, as noted elsewhere the sample support 1618 is often a multi-well plate providing a two-dimensional array of individual wells 1620. Such multi-well plates are available in a variety of standardized formats as to overall dimensions, number of rows and columns, etc. Thus, any given format is associated with a predefined set of well positions. In the operation of the sample analyzing apparatus 1600, the user may provide information accurately identifying the format being utilized to the sample analyzing apparatus 1600, such as by inputting data into or programming the sample analyzing apparatus 1600. This ensures coordination and alignment of moving parts relative to each other, such as between the injector assembly 1636 and the sample support 1618. However, it is possible that the sample analyzing apparatus 1600 may be set up to handle a sample support 1618 of a particular type of format, but the user actually loads a different format onto the sample carrier 1614. For example, the user may load a differently sized sample support, or a sample support providing an incomplete array of wells, i.e., the user may utilize incomplete "strip plates" as appreciated by persons skilled in the art. In such cases, there is a risk that the injector assembly 1636 may dispense liquid directly onto optics components, such as optics components below or proximate to the sample carrier 1614.

In some embodiments, this problem may be addressed by providing a well sensor 1698 in the apparatus housing. The well sensor 1698 may be configured for detecting the presence of individual wells 1620 of the sample support 1618 according to a predefined set of well positions programmed into the sample analyzing apparatus 1600. For this purpose, the well sensor 1698 may be an optical sensor and thus may include a light source for emitting a light beam toward the sample support 1618, and a well sensor detector (i.e., a light detector) for receiving a light beam from the sample support 1618, as schematically depicted by dashed arrows. The light source and well sensor detector may both be located on the same side of the sample support 1618 (and sample carrier 1614), and thus may be contained in the same housing (as illustrated). Alternatively, light source and well sensor detector may be located on opposite sides (e.g., top and bottom) of the sample support 1618 (and sample carrier 1614). Thus, depending on design, the optical signal utilized to interrogate the sample support 1618 may be transmitted through the wells 1620 or reflected from the surface of the wells 1620. In either case, the well sensor detector is optically aligned with the light source so as to receive light emitted from the sample support 1618 in response to light from the light source incident on the sample support 1618. Generally, as appreciated by persons skilled in the art, the well sensor 1698 may be configured for distinguishing the presence or absence of wells 1620 according to a variety of measuring principles such as, for example, measuring the attenuation of the light received by the well sensor detector, sensing a change in refractive index of the surface of the sample support 1618, etc. As an example of operation, after the sample support 1618 has been mounted on the sample carrier 1614, the sample carrier 1614 is moved in an indexed manner relative to the well sensor 1698 to check for the presence of a complete array of wells 1620 and verify that the number and positions of the wells 1620 match with the predefined set of well positions. If the well sensor 1698 determines that one or more wells are missing from the desired format, the well sensor 1698 may cause the analyzing apparatus 1600 to cease operations, such as by transmitting a control signal to the electronics 1688.

Also in the operation of the sample analyzing apparatus 1600, the user may provide information to the sample analyzing apparatus 1600 accurately indicating the amount of reagent or other liquid to be dispensed by the injector needle(s) 1756 and 1758 into each well 1620 of the sample support 1618. The dispensing of precise aliquots may be important for a given type of experiment, and also prevents overfilling of the wells 1620, which may cause spillage and contamination of optics components of the sample analyzing apparatus 1600. It is possible that the user may enter incorrect information as to how much liquid to dispense, or as to how much liquid is already contained in the wells 1620 prior to a subsequent dispensing step, in either case leading to overfilling. In some embodiments, this problem may be addressed by providing a liquid sensor positioned to sense an overfilling event. In some embodiments, the liquid sensor may be integrated with the injector assembly 1636, exploiting the fact that the distal tip of the injector assembly 1636 may be operated in close proximity to the upper surface of the sample support 1618.

Figure 17:
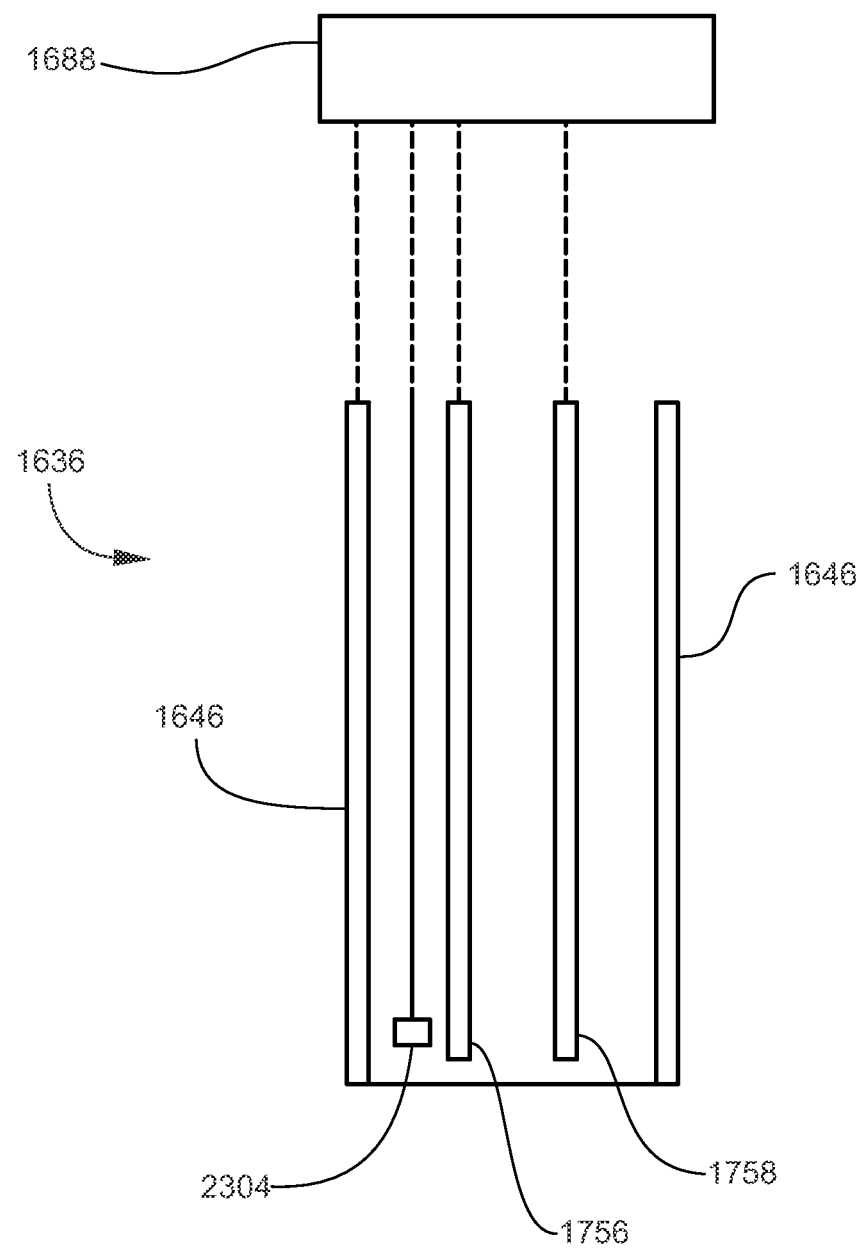
FIG. 17 is a schematic cross-sectional view of an injector or injector/reader assembly and electronics of a luminescence cartridge according to some embodiments.

As examples, FIG. 17 is a schematic cross-sectional view of the injector assembly 1636 and electronics 1688 of the luminescence cartridge 1628. For clarity, the light guide 1754 (FIG. 11) is not shown. In various embodiments, one or more of the injector needles 1756 and 1758 provided, and/or the injector housing 1646, may be utilized as part of the liquid sensor by placing electrically conductive portions of these components in communication with the electronics 1688 using wires as schematically depicted by dashed lines. In this manner, excess liquid on the top of the sample support 1618 may enter the distal tip of the injector housing 1646 and complete an electrical circuit between two of these components, whereby the presence of such liquid may be detected by the electronics 1688 by detecting an electrical current between the two components. In response, the electronics 1688 may cause the sample analysis system 1600 to cease operations.

In one embodiment, the liquid sensor may include a first wire electrically coupled to one of the injector needles 1756 and 1758 at or proximate to the needle outlet, and a second wire electrically coupled to the injector housing 1646 at or proximate to the distal housing end. In this embodiment, an electrical current between the injector needle 1756 or 1758 and the injector housing 1646 indicates the presence of liquid.

In another embodiment, the liquid sensor may include a first wire electrically coupled to the first injector needle 1756 at or proximate to the needle outlet, and a second wire electrically coupled to the second injector needle 1758 at or proximate to the needle outlet. In this embodiment, an electrical current between the injector needles 1756 and 1758 indicates the presence of liquid.

In another embodiment, the liquid sensor may include a first wire electrically coupled to one of the injector needles 1756 and 1758 (or to the injector housing 1646) at or proximate to the needle outlet, and an electrical contact 2304 positioned at or proximate to the needle outlet with a second wire electrically coupled thereto. In this embodiment, an electrical current between the injector needle 1756 or 1758 (or the injector housing 1646) and the electrical contact 2304 indicates the presence of liquid.

Figure 20:
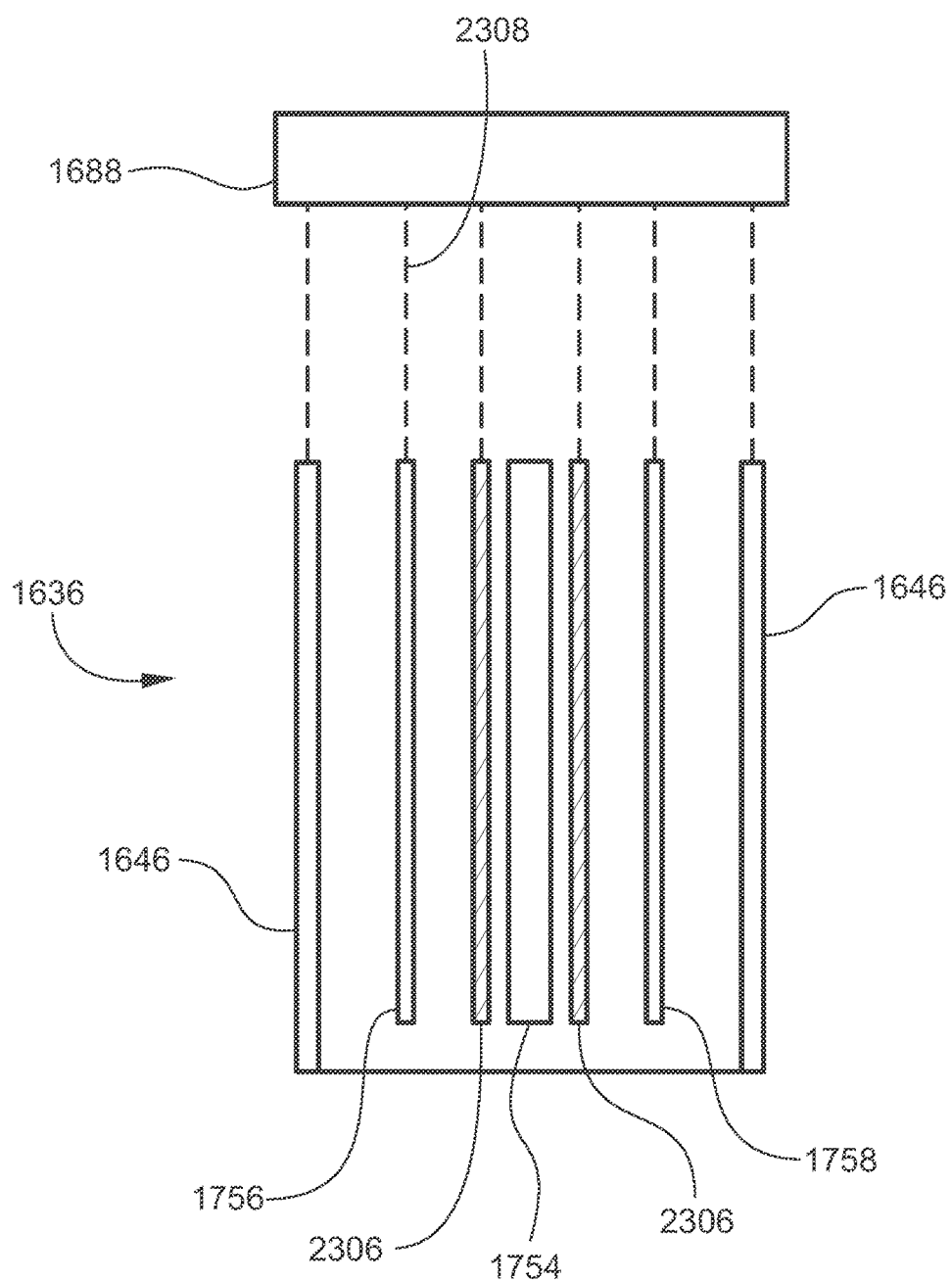
FIG. 20 is a schematic cross-sectional view of another example of an injector or injector/reader assembly and electronics of a luminescence cartridge, according to an embodiment.

FIG. 20 is a schematic cross-sectional view of another example of an injector or injector/reader assembly 1636 and electronics 1688 of a luminescence cartridge. In this embodiment, one of the components of the liquid sensor may be an electrically conductive tube or ring 2306 surrounding the light guide 1754, thus residing between the light guide 1754 and the injector needles 1756 and 1758, and electrically coupled to the electronics 1688 via a wire 2308. The tube or ring 2306 may operate in conjunction with one of the injector needles 1756 and 1758, the injector housing 1646, or the electrical contact 2304 as described above (see FIG. 17) to form the liquid sensor.

Another problem occurs when the sample analyzing apparatus 1600 is set up to handle a sample support 1618 of a particular type of format, but the user actually loads onto the sample carrier 1614 a sample support having a plate height that is different from what has been programmed into the sample analyzing apparatus 1600. If the plate height is lower than the expected height, then the distance or gap between the tip(s) of the injector needle(s) 1756 and 1758 and the wells 1620 of the sample support 1618 (i.e., the upper surface, or top, of the sample support 1618) will be too large at the normal dispensing position of the injector assembly 1636. This creates the risk of liquid dispensed from the injector assembly 1636 contaminating wells adjacent to the target well and/or contaminating optics proximate to or below the sample support 1618. In some embodiments, this problem may be addressed by providing a gap sensor positioned and configured for measuring the gap between the tip of the injector assembly 1636 and the top of the sample support 1618.

Figure 18:
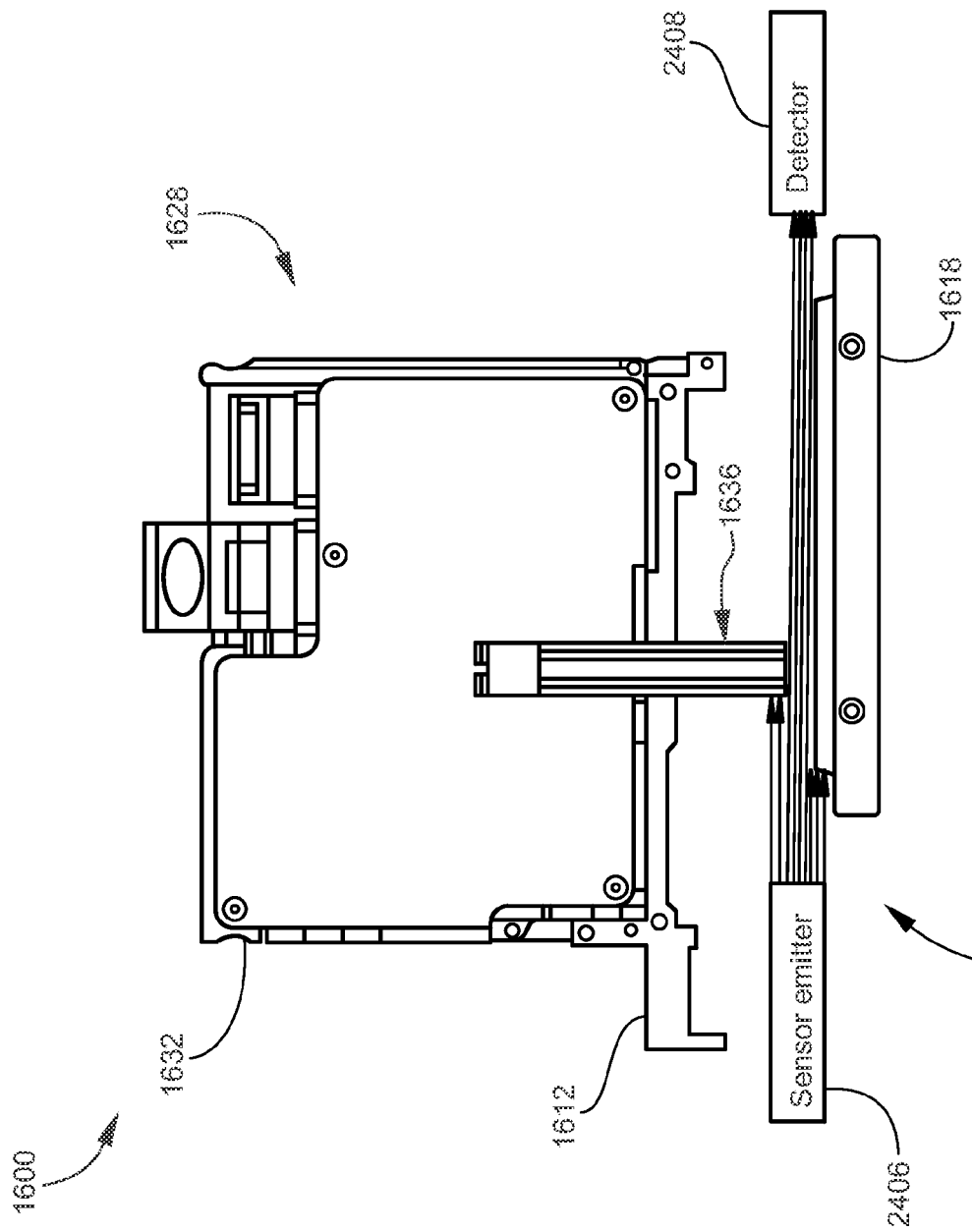
FIG. 18 is an elevation view of the sample analyzing apparatus illustrated in FIG. 10 in which a gap sensor is provided in the apparatus housing below a luminescence cartridge.

As an example, FIG. 18 is an elevation view of the sample analyzing apparatus 1600 in which a gap sensor 2404 is provided in the apparatus housing below the luminescence cartridge 1628. The gap sensor 2404 includes a light source 2406 and a gap sensor detector 2408 (i.e., a light detector) optically aligned with the light source 2406. The light source 2406 and the gap sensor detector 2408 may be positioned on opposite sides of the sample support 1618, with the optical axis between the light source 2406 and the gap sensor detector 2408 being oriented in the transverse (horizontal) plane. By this configuration and as illustrated, the light source 2406 is configured for emitting a light beam through the gap and incident on the tip and the sample support. In this manner, the gap may be measured, such as by measuring the difference in elevation between the tip of the injector assembly 1636 and the top of the sample support 1618, or by measuring the elevation of the top of the sample support 1618 relative to a known reference datum. If the measured gap exceeds some threshold value, the gap sensor 2404 may be configured to output a control signal that causes the sample analysis system 1600 to cease operations. In some embodiments, the gap sensor 2404 may also be utilized to measure the elevation of the tip of the injector assembly 1636 relative to a known reference datum, for the purpose of verifying that the injector assembly 1636 has been extended to a desired operating position in close proximity to the sample support 1618.

Another problem that may occur unexpectedly or during the normal course operation of the injector system is that a fluid line (e.g., tubing) or fluidic fitting may malfunction and cause liquid to leak into the interior of the cartridge housing 1632. Such an event may potentially contaminate one or more components of the luminescence cartridge 1628. In some embodiments, this problem may be addressed by providing a liquid sensor (or leak sensor) configured for detecting liquid accumulating in a bottom section of the cartridge housing 1632.

Figure 19:
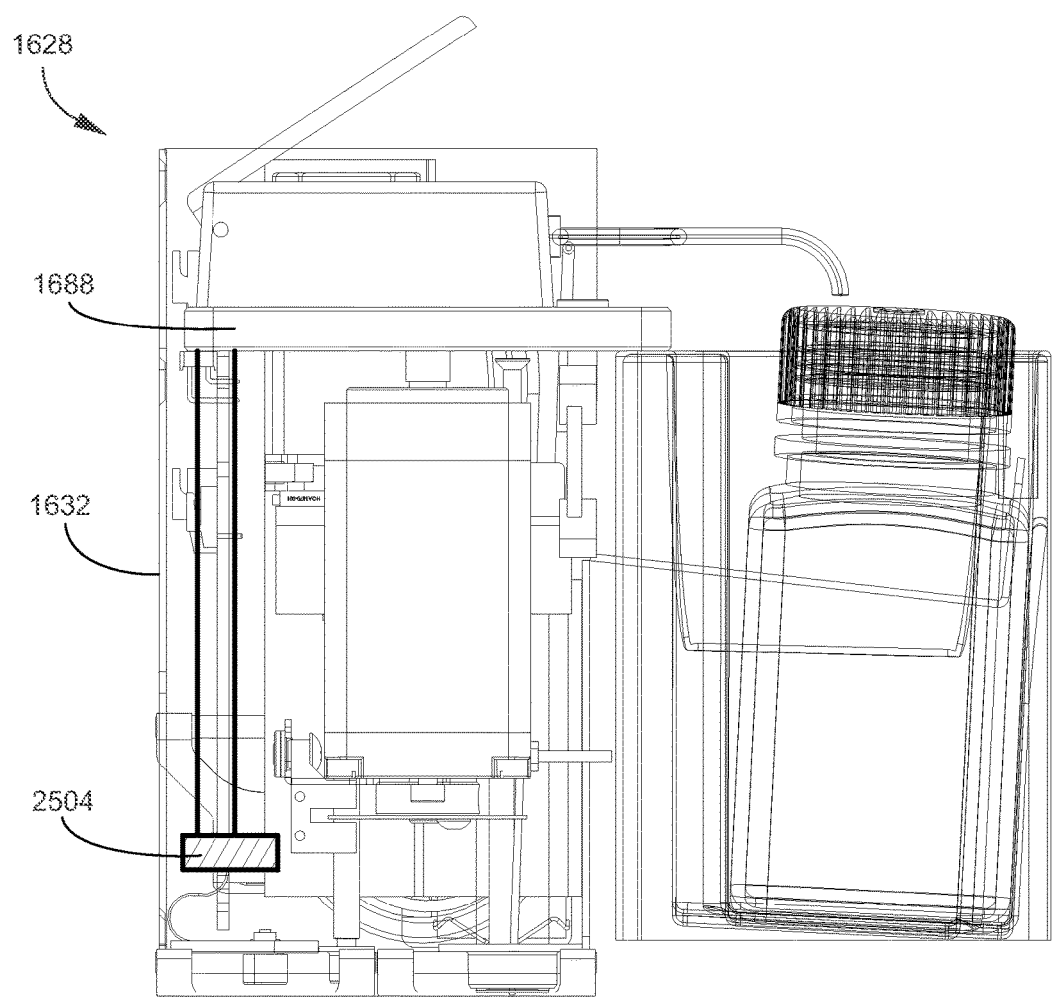
FIG. 19 is an elevation view of a luminescence cartridge in which a liquid sensor is provided in a cartridge housing according to some embodiments.

As an example, FIG. 19 is an elevation view of the luminescence cartridge 1628 in which a liquid sensor 2504 is provided in the cartridge housing 1632. The cartridge housing 1632 may be constructed in a liquid-tight manner and sized to potentially hold the equivalent of at least one reagent reservoir 1672 or 1674 (FIG. 10). The liquid sensor 2504 may be positioned at or near a bottom wall of the cartridge housing 1632. In some embodiments, the liquid sensor 2504 may be a capacitive sensor positioned at the bottom wall and communicating with the electronics 1688 via wires. The conductive components of the liquid sensor 2504 may be encapsulated between a substrate such as a PCB and a thin insulating layer to protect the conductive components from exposure to liquid. The liquid sensor 2504 may be sensitive to liquid contacting the liquid sensor 2504, as manifested by a change in capacitance. The electronics 1688 may be configured for detecting a change in capacitance resulting from the presence of leaking liquid on the capacitive sensor, and in response cause the sample analysis system 1600 to cease operations.

According to another embodiment of the present invention, a method for analyzing a target in a sample is provided. According to this embodiment, a cartridge system having a cartridge support and one or more cartridges that are removably engaged with a cartridge support is selected. The cartridges may be one or more of the cartridges described herein. Then, a first cartridge contained within the cartridge system is selected. A second cartridge, i.e., a new or replacement cartridge, not contained within the cartridge system is then selected. The first cartridge is then replaced with the second cartridge and a target in a sample is analyzed with the second cartridge. In some embodiments, the first cartridge may be removed from the apparatus and replaced with the second cartridge without the use of mechanical tools, and after the first cartridge is replaced with the second cartridge, the system is instructed, with apparatus-readable instructions, with information for analyzing the target in the sample.

According to other embodiments, the sample analyzing apparatus is an optical reader system that does not utilize cartridges, i.e., the sample analyzing apparatus is a non-cartridge based sample analyzing apparatus. The configuration of the sample analyzing apparatus may be dedicated for luminescence-based measurement techniques. Alternatively, the sample analyzing apparatus may be reconfigurable for implementing different types of measurement techniques (e.g., luminescence, absorbance, fluorescence, etc.). For luminescence measurement entailing the use of a liquid injector system, one or more components of the liquid injector system may be removably mounted in the apparatus housing of the sample analyzing apparatus. For this purpose, a user may access the interior of the apparatus housing via a top panel (lid) or other panel or door of the apparatus housing. In such embodiments, instead of providing a cartridge support, the sample analyzing apparatus may include mounting features in the apparatus housing for mounting components of the injector system, including an injector assembly (which may be configured as described above, with or without an integral light guide), one or more pumps, liquid lines, and reagent reservoirs. The sample analyzing apparatus may also include a movable sample carrier for supporting one or more samples (or for supporting a sample support that holds or contains such samples, such as a multi-well plate) as described above. The sample analyzing apparatus may also include one or more optical detectors, as well as electronics communicating with various bubble and liquid sensors, as described above. Generally, the structure and operation of any or all of the foregoing components of the sample analyzing apparatus may be consistent with those described above in conjunction with other embodiments disclosed herein. For example, FIGS. 10 to 18 may be considered as generally representative of such a sample analyzing apparatus, with the understanding various components would be positioned directly in the apparatus housing instead of in a cartridge. In such embodiments, the injector assembly may be mounted in a fixed position and the sample carrier may be moved to properly position the sample relative to the injector assembly. Thus, a driver for moving the injector assembly as described above need not be provided. In embodiments where the injector assembly does not include a light guide, a bottom read head as described above may be utilized.

In embodiments of the non-cartridge based sample analyzing apparatus, rinsing and priming may again be performed outside of the apparatus housing, by removing the injector assembly and other components of the injector system as needed to avoid dispensing liquid or liquid/air mixtures onto sensitive components in the interior of the apparatus housing. After the injector assembly has been moved to an outside position, an external rinsing/priming station including an external liquid container may be utilized in a manner analogous to the cartridge-based embodiments described above. The non-cartridge based sample analyzing apparatus may also include one or more of the sensors and liquid dispensing control features described above in conjunction with FIGS. 10-18, such as the capacitive bubble sensors 1692, 1694, and 2200, the electrical grounding features described above in conjunction with FIG. 16, the well sensor 1698, the use of the injector assembly as a liquid sensor to prevent overfilling of sample wells, and the gap sensor 2404.

Exemplary Embodiments

Exemplary embodiments provided in accordance with the presently disclosed subject matter include, but are not limited to, the following:

1. A sample analyzing apparatus, comprising: an apparatus housing; a sample carrier disposed in the apparatus housing and configured for supporting a sample; a reagent reservoir; a pump communicating with the reagent reservoir; an injector assembly disposed in the apparatus housing and comprising an injector housing and an injector needle extending through the injector housing and configured for communicating with the reagent reservoir via the pump; and a luminescence detector positioned in the apparatus housing to receive optical signals from the sample.

2. The sample analyzing apparatus of embodiment 1, wherein the sample carrier is movable to align the injector assembly with a sample contained on the sample carrier.

3. The sample analyzing apparatus of embodiment 1, comprising a luminescence cartridge removably mounted at the sample analyzing apparatus, the luminescence cartridge comprising a cartridge housing comprising a cartridge housing opening, and a driver disposed in the cartridge housing, wherein the reservoir support and the pump are disposed in the cartridge housing, and the injector assembly is at least partially disposed in the cartridge housing and is movable by the driver through the cartridge housing opening and alternately toward and away from the sample carrier.

4. The sample analyzing apparatus of embodiment 3, wherein the luminescence cartridge comprises an electrical connector mounted at the cartridge housing and in signal communication with the driver and the pump, the electrical connector configured for removable coupling to the sample analyzing apparatus to receive power from and transmit signals to or from the sample analyzing apparatus.

5. The sample analyzing apparatus of embodiment 4, comprising a feature disposed in the apparatus housing and communicating with the electrical connector when the luminescence cartridge is removably mounted at the sample analyzing apparatus, the feature selected from the group consisting of: a power source; signal processing circuitry configured for receiving detection signals from the luminescence detector; a drive controller configured for transmitting control signals to the driver; a pump controller configured for transmitting control signals to the pump; and a combination of two or more of the foregoing.

6. The sample analyzing apparatus of embodiment 3, wherein the injector assembly comprises a light guide extending through the injector housing and configured for communicating with the luminescence detector.

7. The sample analyzing apparatus of embodiment 6, wherein the luminescence detector is disposed in the cartridge housing.

8. The sample analyzing apparatus of embodiment 6, wherein the cartridge housing comprises an optical output port, and the light guide is coupled to or extends through the optical output port.

9. The sample analyzing apparatus of embodiment 6, wherein the injector housing comprises a distal housing end, the injector needle comprises a needle outlet at the distal housing end, and the injector assembly comprises a liquid sensor configured for detecting liquid at the housing end, the liquid sensor comprising an electrically conductive tube surrounding the light guide and configured for communicating with electronics configured for detecting an electrical current between the electrically conductive tube and the injector needle or between the electrically conductive tube and the injector housing.

10. The sample analyzing apparatus of embodiment 3, wherein the reservoir support is movable between an inside reservoir support position at which the reservoir support is positioned entirely in the cartridge housing and an outside reservoir support position at which the reservoir support is positioned at least partially outside the cartridge housing.

11. The sample analyzing apparatus of embodiment 3, comprising a liquid sensor configured for detecting liquid accumulating in a bottom section of the cartridge housing.

12. The sample analyzing apparatus of embodiment 11, wherein the cartridge housing comprises a bottom wall through which the cartridge housing opening is formed, and the liquid sensor comprises a capacitive sensor positioned at the bottom wall and configured for communicating with electronics configured for detecting a signal from the capacitive sensor indicative of the presence of liquid on the capacitive sensor.

13. The sample analyzing apparatus of embodiment 3, comprising a cartridge support configured for receiving the luminescence cartridge such that the luminescence cartridge is removably mounted thereto, the cartridge support movable between an inside cartridge support position at which the cartridge support is positioned entirely in the apparatus housing and an outside cartridge support position at which the cartridge support is positioned at least partially outside the apparatus housing.

14. The sample analyzing apparatus of embodiment 13, wherein the cartridge support is movable to align the injector assembly with a sample contained on the sample carrier.

15. The sample analyzing apparatus of embodiment 13, wherein the cartridge support comprises a plurality of cartridge positions configured for receiving the luminescence cartridge and one or more other removable cartridges concurrently.

16. The sample analyzing apparatus of embodiment 13, wherein the apparatus housing comprises an outer wall having an apparatus housing opening through which the cartridge support is movable along a first direction between the inside cartridge support position and the outside cartridge support position.

17. The sample analyzing apparatus of embodiment 16, wherein the reservoir support is movable along a second direction perpendicular to the first direction, between an inside reservoir support position at which the reservoir support is positioned entirely in the cartridge housing and an outside reservoir support position at which the reservoir support is positioned at least partially outside the cartridge housing.

18. The sample analyzing apparatus of embodiment 17, wherein the reservoir support is movable to the outside reservoir support position when the cartridge support is at the outside cartridge support position, and at the outside reservoir support position the reservoir support is in an overlapping relation with the outer wall such that the reservoir support prevents the cartridge support from being moved to the inside cartridge support position.

19. The sample analyzing apparatus of embodiment 13, comprising an external liquid container removably mountable to at least one of the luminescence cartridge and the cartridge support while the cartridge support is at the outside cartridge support position, the external liquid container comprising a port configured for receiving the injector assembly, wherein the injector assembly is movable by the driver alternately into and out from the port.

20. The sample analyzing apparatus of embodiment 19, wherein the apparatus housing comprises an outer wall having an apparatus housing opening through which the cartridge support is movable between the inside cartridge support position and the outside cartridge support position, and the external liquid container is configured for overlapping with the outer wall when the external liquid container is mounted to the luminescence cartridge or the cartridge support, such that the external liquid container prevents the cartridge support from being moved to the inside cartridge support position.

21. The sample analyzing apparatus of embodiment 1, comprising a well sensor configured for detecting the presence of individual wells of a sample support disposed on the sample carrier according to a predefined set of well positions, wherein the sample carrier is movable to align the sample support sensor with each well position.

22. The sample analyzing apparatus of embodiment 21, wherein the well sensor comprises a light source and a well sensor detector aligned with the light source, and wherein either or both of the light source and the well sensor are positioned above or below the sample carrier.

23. The sample analyzing apparatus of embodiment 1, comprising a gap sensor configured for measuring a gap between a tip of the injector assembly and a top of a sample support disposed on the sample carrier.

24. The sample analyzing apparatus of embodiment 23, wherein the gap sensor comprises a light source and a gap sensor detector aligned with the light source, and the light source configured for emitting a light beam through the gap and incident on the tip and the sample support.

25. The sample analyzing apparatus of embodiment 1, wherein the injector needle is a first injector needle configured for communicating with a first reagent reservoir, and the injector assembly further comprises a second injector needle extending through the injector housing and configured for communicating with a second reagent reservoir supported by the reservoir support via the pump.

26. The sample analyzing apparatus of embodiment 1, wherein the injector needle has a configuration selected from the group consisting of: the injector needle is composed of an electrically conductive material and communicates with an electrical ground; the injector needle is composed of an electrically conductive material and communicates with an electrical ground, and the injector needle comprises an inside surface and a non-metallic coating on the inside surface, wherein the inside surface comprises an uncovered region not covered by the non-metal coating such that liquid flowing through the injector needle is exposed to the uncovered region; the injector needle is composed of an electrically conductive material and communicates with an electrical ground, and the injector needle comprises an inside surface and a non-metallic, electrically conductive coating on the inside surface; at least a portion of the injector needle is composed of or coated with an antistatic plastic and communicates with an electrical ground, wherein liquid flowing through the injector needle is exposed to the antistatic plastic; and the sample analyzing apparatus comprises a plastic tube fluidly coupled between the pump and the injector needle, the plastic tube is composed of or coated with an antistatic plastic and communicating with an electrical ground, wherein liquid flowing through the injector needle is exposed to the antistatic plastic.

27. The sample analyzing apparatus of embodiment 1, comprising a tube fluidly coupled between the pump and the injector needle, and a bubble sensor configured for detecting a bubble in the tube.

28. The sample analyzing apparatus of embodiment 1, wherein the injector housing comprises a distal housing end, the injector needle comprises a needle outlet at the distal housing end, and the injector assembly comprises a liquid sensor disposed in the injector housing and configured for detecting liquid at the housing end.

29. The sample analyzing apparatus of embodiment 1, wherein the injector housing comprises a distal housing end, the injector needle comprises a needle outlet at the distal housing end, and the injector assembly comprises a liquid sensor disposed in the injector housing and configured for detecting liquid at the housing end.

30. The sample analyzing apparatus of embodiment 29, wherein the liquid sensor has a configuration selected from the group consisting of: the liquid sensor comprises a first wire electrically coupled to the injector needle at or proximate to the needle outlet, and a second wire electrically coupled to the injector housing at or proximate to the distal housing end, wherein the first wire and the second wire are configured for communicating with electronics configured for detecting an electrical current between the injector needle and the injector housing; the liquid sensor comprises an electrical contact positioned at the same or substantially the same elevation as the needle outlet, a first wire electrically coupled to the electrical contact, and a second wire electrically coupled to the injector needle at or proximate to the needle outlet or to the injector housing at or proximate to the distal housing end, wherein the first wire and the second wire are configured for communicating with electronics configured for detecting an electrical current between the electrical contact and the injector needle or between the electrical contact and the injector housing; wherein the injector needle is a first injector needle, the needle outlet is a first needle outlet, and the injector assembly further comprises a second injector needle extending through the injector housing comprising a second needle outlet, and the liquid sensor comprises a first wire electrically coupled to the first injector needle at or proximate to the first needle outlet, and a second wire electrically coupled to the second injector needle at or proximate to the second needle outlet, wherein the first wire and the second wire are configured for communicating with electronics configured for detecting an electrical current between the first injector needle and the second injector needle; the liquid sensor comprises an electrically conductive tube configured for communicating with electronics configured for detecting an electrical current between the electrically conductive tube and the injector needle or between the electrically conductive tube and the injector housing.

31. A luminescence cartridge for use in a sample analyzing apparatus, the luminescence cartridge comprising: a cartridge housing comprising a cartridge housing opening; a reservoir support disposed in the cartridge housing and configured for supporting a reagent reservoir; a pump communicating with the reagent reservoir; a driver disposed in the cartridge housing; an injector/reader assembly at least partially disposed in the cartridge housing and comprising an injector/reader housing, an injector needle extending through the injector/reader housing and configured for communicating with a reagent reservoir supported by the reservoir support via the pump, and a light guide extending through the injector/reader housing and configured for communicating with a luminescence detector, wherein the injector/reader assembly is movable by the driver through the cartridge housing opening and alternately toward and away from the cartridge housing; and an electrical connector mounted at the cartridge housing and in signal communication with the driver and the pump, the electrical connector configured for removable coupling to the sample analyzing apparatus to receive power from and transmit signals to or from the sample analyzing apparatus.

32. A sample analyzing apparatus, comprising: the luminescence cartridge of embodiment 31; an apparatus housing; a sample carrier disposed in the apparatus housing; and a cartridge support configured for receiving the luminescence cartridge such that the luminescence cartridge is removably mounted thereto, the cartridge support movable between an inside cartridge support position at which the cartridge support is positioned entirely in the apparatus housing and an outside cartridge support position at which the cartridge support is positioned at least partially outside the apparatus housing, wherein: the injector/reader assembly is movable by the driver alternately toward and away from the sample carrier; and at least one of the sample carrier and the cartridge support is movable to align the injector/reader assembly with a sample contained on the sample carrier.

33. The sample analyzing apparatus of embodiment 32, comprising an external liquid container removably mountable to at least one of the luminescence cartridge and the cartridge support while the cartridge support is at the outside cartridge support position, the external liquid container comprising a port configured for receiving the injector/reader assembly, wherein the injector/reader assembly is movable by the driver alternately into and out from the port.

34. A method for analyzing a sample, the method comprising: positioning an injector assembly in alignment with and at a desired distance from a sample in a sample analyzing apparatus, the injector assembly comprising an injector housing and an injector needle extending through the injector housing; injecting a reagent from the injector needle to the sample by operating the pump to establish a flow of the reagent from a reagent reservoir to the injector needle; and detecting luminescent light emitted from the sample at a luminescence detector.

35. The method of embodiment 34, comprising moving the injector assembly to the desired distance from the sample by operating a driver in the sample analyzing apparatus.

36. The method of embodiment 34, wherein positioning the injector assembly comprises moving a sample carrier on which the sample is supported.

37. The method of embodiment 34, wherein the injector needle is a first injector needle configured for communicating with a first reagent reservoir for injecting a first reagent, and the injector assembly further comprises a second injector needle extending through the injector housing and communicating with a second reagent reservoir supported by the reservoir support via the pump, and further comprising: after injecting the first reagent and receiving luminescent light, injecting a second reagent from the second injector needle, and transmitting to the luminescence detector luminescent light emitted from the sample in response to injecting the second reagent.

38. The method of embodiment 37, wherein the first reagent comprises firefly luciferase and the second reagent comprises *Renilla* luciferase.

39. The method of embodiment 34, comprising electrically grounding the injector needle, or electrically grounding a tube fluidly coupled between the pump and the injector needle, to suppress static electricity in liquid flowing through the injector needle.

40. The method of embodiment 34, comprising removing the injector assembly from the sample analyzing apparatus, and performing a rinsing or priming operation by flowing a liquid through the injector needle while the injector assembly is outside of the sample analyzing apparatus.

41. The method of embodiment 40, comprising placing an external liquid source in fluid communication with the pump, placing an external liquid container in fluid communication with the injector needle, and flowing the liquid through the injector needle and into the external liquid container by operating the pump.

42. The method of embodiment 41, wherein placing the external liquid container in fluid communication with the injector needle comprises moving the injector assembly into a port of the external liquid container.

43. The method of embodiment 34, comprising monitoring a tube fluidly coupled between the pump and the injector needle for the presence of a bubble in the tube.

44. The method of embodiment 34, wherein the sample is supported on a multi-well sample support, and comprising operating a well sensor to determine whether the multi-well sample support is configured according to a predefined set of well positions.

45. The method of embodiment 34, comprising operating a liquid sensor in the injector housing to detect for the presence of liquid in the injector housing outside of the injector needle.

46. The method of embodiment 34, comprising operating a gap sensor to measure a gap between a tip of the injector assembly and a top of a sample support at which the sample is supported.

47. The method of embodiment 34, wherein the sample analyzing apparatus comprises a cartridge support, and further comprising: loading a luminescence cartridge on the cartridge support, wherein the luminescence cartridge comprises a cartridge housing comprising a cartridge housing opening, the pump and the reagent reservoir are disposed in the cartridge housing, and the injector assembly is at least partially disposed in the cartridge housing and extends through the cartridge housing opening; and before aligning the injector assembly with the sample, moving the luminescence cartridge into an apparatus housing of the apparatus by operating the cartridge support.

48. The method of embodiment 47, comprising moving the injector assembly to the desired distance from the sample by operating a driver in the cartridge housing.

49. The method of embodiment 47, wherein positioning the injector assembly comprises moving the cartridge support, moving a sample carrier on which the sample is supported, or both of the foregoing.

50. The method of embodiment 47, comprising performing a rinsing or priming operation by flowing a liquid through the injector needle while the injector assembly remains assembled in the cartridge housing and while the cartridge housing is at least partially outside of an apparatus housing of the sample analyzing apparatus.

51. The method of embodiment 47, comprising moving the luminescence cartridge to an outside position at which the luminescence cartridge is at least partially outside of an apparatus housing of the sample analyzing apparatus by operating the cartridge support, placing an external liquid source in fluid communication with the pump, placing an external liquid container in fluid communication with the injector needle, and flowing a liquid through the injector needle and into the external liquid container by operating the pump.

52. The method of embodiment 51, wherein placing the external liquid container in fluid communication with the injector needle comprises moving the injector assembly into a port of the external liquid container.

53. The method of embodiment 51, comprising, while the luminescence cartridge is at the outside position, preventing the luminescence cartridge from being moved into the apparatus housing.

54. The method of embodiment 53, wherein preventing comprises at least one of the following: moving a reservoir support on which the reagent reservoir is supported in the cartridge housing to a position at which the reservoir support is in an overlapping relation with an outer wall of the apparatus housing; or mounting the external liquid container to the luminescence cartridge or the cartridge support such that the external liquid container is in an overlapping relation with an outer wall of the apparatus housing.

55. The method of embodiment 47, comprising operating a liquid sensor to detect for the presence of liquid accumulating in a bottom section of the cartridge housing.

It will be understood that one or more of the processes, sub-processes, and process steps described herein may be performed by hardware, firmware, software, or a combination of two or more of the foregoing, on one or more electronic or digitally-controlled devices. The software may reside in a software memory (not shown) in a suitable electronic processing component or system such as, for example, the system controller 74 schematically depicted in FIG. 3. The software memory may include an ordered listing of executable instructions for implementing logical functions (that is, "logic" that may be implemented in digital form such as digital circuitry or source code, or in analog form such as an analog source such as an analog electrical, sound, or video signal). The instructions may be executed within a processing module, which includes, for example, one or more microprocessors, general purpose processors, combinations of processors, digital signal processors (DSPs), or application specific integrated circuits (ASICs). Further, the schematic diagrams describe a logical division of functions having physical (hardware and/or software) implementations that are not limited by architecture or the physical layout of the functions. The examples of systems described herein may be implemented in a variety of configurations and operate as hardware/software components in a single hardware/software unit, or in separate hardware/software units.

The executable instructions may be implemented as a computer program product having instructions stored therein which, when executed by a processing module of an electronic system (e.g., the system controller 74 in FIG. 3), direct the electronic system to carry out the instructions. The computer program product may be selectively embodied in any non-transitory computer-readable storage medium for use by or in connection with an instruction execution system, apparatus, or device, such as a electronic computer-based system, processor-containing system, or other system that may selectively fetch the instructions from the instruction execution system, apparatus, or device and execute the instructions. In the context of this disclosure, a computer-readable storage medium is any non-transitory means that may store the program for use by or in connection with the instruction execution system, apparatus, or device. The non-transitory computer-readable storage medium may selectively be, for example, an electronic, magnetic, optical, electromagnetic, infrared, or semiconductor system, apparatus, or device. A non-exhaustive list of more specific examples of non-transitory computer readable media include: an electrical connection having one or more wires (electronic); a portable computer diskette (magnetic); a random access memory (electronic); a read-only memory (electronic); an erasable programmable read only memory such as, for example, flash memory (electronic); a compact disc memory such as, for example, CD-ROM, CD-R, CD-RW (optical); and digital versatile disc memory, i.e., DVD (optical). Note that the non-transitory computer-readable storage medium may even be paper or another suitable medium upon which the program is printed, as the program can be electronically captured via, for instance, optical scanning of the paper or other medium, then compiled, interpreted, or otherwise processed in a suitable manner if necessary, and then stored in a computer memory or machine memory.

It will also be understood that the term "in signal communication" as used herein means that two or more systems, devices, components, modules, or sub-modules are capable of communicating with each other via signals that travel over some type of signal path. The signals may be communication, power, data, or energy signals, which may communicate information, power, or energy from a first system, device, component, module, or sub-module to a second system, device, component, module, or sub-module along a signal path between the first and second system, device, component, module, or sub-module. The signal paths may include physical, electrical, magnetic, electromagnetic, electrochemical, optical, wired, or wireless connections. The signal paths may also include additional systems, devices, components, modules, or sub-modules between the first and second system, device, component, module, or sub-module.

More generally, terms such as "communicate" and "in . . . communication with" (for example, a first component "communicates with" or "is in communication with" a second component) are used herein to indicate a structural, functional, mechanical, electrical, signal, optical, magnetic, electromagnetic, ionic or fluidic relationship between two or more components or elements. As such, the fact that one component is said to communicate with a second component is not intended to exclude the possibility that additional components may be present between, and/or operatively associated or engaged with, the first and second components.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. A sample analyzing apparatus, comprising:
   an apparatus housing;
   a sample carrier disposed in the apparatus housing and configured for supporting a sample;
   a reservoir support configured for supporting a reagent reservoir;
   a pump configured for communicating with the reagent reservoir;
   an injector assembly disposed in the apparatus housing, and comprising an injector housing and an injector needle extending through the injector housing and configured for communicating with the reagent reservoir via the pump;
   a driver configured for moving the injector assembly toward and away from the sample carrier; and
   a luminescence detector positioned in the apparatus housing to receive optical signals from the sample, wherein:
   the injector housing comprises a distal housing end, the injector needle comprises a needle outlet at the distal housing end, and the injector assembly comprises a liquid sensor disposed in the injector housing and configured for detecting liquid at the housing end; and
   the injector assembly has a configuration selected from the group consisting of:
     the liquid sensor comprises a first wire electrically coupled to the injector needle at or proximate to the needle outlet, and a second wire electrically coupled to the injector housing at or proximate to the distal housing end, wherein the first wire and the second wire are configured for communicating with electronics configured for detecting an electrical current between the injector needle and the injector housing;
     the liquid sensor comprises an electrical contact positioned at the same or substantially the same elevation as the needle outlet, a first wire electrically coupled to the electrical contact, and a second wire electrically coupled to the injector needle at or proximate to the needle outlet or to the injector housing at or proximate to the distal housing end, wherein the first wire and the second wire are configured for communicating with electronics configured for detecting an electrical current between the electrical contact and the injector needle or between the electrical contact and the injector housing;
     the injector needle is a first injector needle, the needle outlet is a first needle outlet, and the injector assembly further comprises a second injector needle extending through the injector housing comprising a second needle outlet, and the liquid sensor comprises a first wire electrically coupled to the first injector needle at or proximate to the first needle outlet, and a second wire electrically coupled to the second injector needle at or proximate to the second needle outlet, wherein the first wire and the second wire are configured for communicating with electronics configured for detecting an electrical current between the first injector needle and the second injector needle; and
     the liquid sensor comprises an electrically conductive tube configured for communicating with electronics configured for detecting an electrical current between the electrically conductive tube and the injector needle or between the electrically conductive tube and the injector housing.

2. The sample analyzing apparatus of claim 1, wherein the sample carrier is movable to align the injector assembly with a sample contained on the sample carrier.

3. The sample analyzing apparatus of claim 1, comprising a luminescence cartridge removably mounted at the sample analyzing apparatus, the luminescence cartridge comprising a cartridge housing comprising a cartridge housing opening, wherein the driver, the reservoir support and the pump are disposed in the cartridge housing, and the injector assembly is at least partially disposed in the cartridge housing and is movable by the driver through the cartridge housing opening and alternately toward and away from the sample carrier.

4. The sample analyzing apparatus of claim 3, wherein the luminescence cartridge comprises an electrical connector mounted at the cartridge housing and in signal communication with the driver and the pump, the electrical connector configured for removable coupling to the sample analyzing apparatus to receive power from and transmit signals to or from the sample analyzing apparatus.

5. The sample analyzing apparatus of claim 4, comprising a feature disposed in the apparatus housing and communicating with the electrical connector when the luminescence cartridge is removably mounted at the sample analyzing apparatus, the feature selected from the group consisting of: a power source; signal processing circuitry configured for receiving detection signals from the luminescence detector; a drive controller configured for transmitting control signals to the driver; a pump controller configured for transmitting control signals to the pump; and a combination of two or more of the foregoing.

6. The sample analyzing apparatus of claim 3, wherein the luminescence detector is disposed in the cartridge housing.

7. The sample analyzing apparatus of claim 3, wherein the injector assembly comprises a light guide extending through the injector housing and configured for communicating with the luminescence detector, the cartridge housing comprises an optical output port, and the light guide is coupled to or extends through the optical output port.

8. The sample analyzing apparatus of claim 3, wherein the reservoir support is movable between an inside reservoir support position at which the reservoir support is positioned entirely in the cartridge housing and an outside reservoir support position at which the reservoir support is positioned at least partially outside the cartridge housing.

9. The sample analyzing apparatus of claim 3, comprising an additional liquid sensor configured for detecting liquid accumulating in a bottom section of the cartridge housing.

10. The sample analyzing apparatus of claim 9, wherein the cartridge housing comprises a bottom wall through which the cartridge housing opening is formed, and the additional liquid sensor comprises a capacitive sensor positioned at the bottom wall and configured for communicating with electronics configured for detecting a signal from the capacitive sensor indicative of the presence of liquid on the capacitive sensor.

11. The sample analyzing apparatus of claim 3, comprising a cartridge support configured for receiving the luminescence cartridge such that the luminescence cartridge is removably mounted thereto, the cartridge support movable between an inside cartridge support position at which the cartridge support is positioned entirely in the apparatus housing and an outside cartridge support position at which the cartridge support is positioned at least partially outside the apparatus housing.

12. The sample analyzing apparatus of claim 11, wherein the cartridge support is movable to align the injector assembly with a sample contained on the sample carrier.

13. The sample analyzing apparatus of claim 11, wherein the cartridge support comprises a plurality of cartridge positions configured for receiving the luminescence cartridge and one or more other removable cartridges concurrently.

14. The sample analyzing apparatus of claim 11, wherein the apparatus housing comprises an outer wall having an apparatus housing opening through which the cartridge support is movable along a first direction between the inside cartridge support position and the outside cartridge support position.

15. The sample analyzing apparatus of claim 14, wherein the reservoir support is movable along a second direction perpendicular to the first direction, between an inside reservoir support position at which the reservoir support is positioned entirely in the cartridge housing and an outside reservoir support position at which the reservoir support is positioned at least partially outside the cartridge housing.

16. The sample analyzing apparatus of claim 15, wherein the reservoir support is movable to the outside reservoir support position when the cartridge support is at the outside cartridge support position, and at the outside reservoir support position the reservoir support is in an overlapping relation with the outer wall such that the reservoir support prevents the cartridge support from being moved to the inside cartridge support position.

17. The sample analyzing apparatus of claim 11, comprising an external liquid container removably mountable to at least one of the luminescence cartridge and the cartridge support while the cartridge support is at the outside cartridge support position, the external liquid container comprising a port configured for receiving the injector assembly, wherein the injector assembly is movable by the driver alternately into and out from the port.

18. The sample analyzing apparatus of claim 17, wherein the apparatus housing comprises an outer wall having an apparatus housing opening through which the cartridge support is movable between the inside cartridge support position and the outside cartridge support position, and the external liquid container is configured for overlapping with the outer wall when the external liquid container is mounted to the luminescence cartridge or the cartridge support, such that the external liquid container prevents the cartridge support from being moved to the inside cartridge support position.

19. The sample analyzing apparatus of claim 1, comprising a well sensor configured for detecting the presence of individual wells of a sample support disposed on the sample carrier according to a predefined set of well positions, wherein the sample carrier is movable to align the sample support sensor with each well position.

20. The sample analyzing apparatus of claim 19, wherein the well sensor comprises a light source and a well sensor detector aligned with the light source, and wherein either or both of the light source and the well sensor detector are positioned above or below the sample carrier.

21. The sample analyzing apparatus of claim 1, comprising a gap sensor configured for measuring a gap between a tip of the injector assembly and a top of a sample support disposed on the sample carrier.

22. The sample analyzing apparatus of claim 21, wherein the gap sensor comprises a light source and a gap sensor detector aligned with the light source, and the light source configured for emitting a light beam through the gap and incident on the tip and the sample support.

23. The sample analyzing apparatus of claim 1, wherein the injector needle has a configuration selected from the group consisting of:
the injector needle is composed of an electrically conductive material and communicates with an electrical ground;
the injector needle is composed of an electrically conductive material and communicates with an electrical ground, and the injector needle comprises an inside surface and a non-metallic coating on the inside surface, wherein the inside surface comprises an uncovered region not covered by the non-metallic coating such that liquid flowing through the injector needle is exposed to the uncovered region;
the injector needle is composed of an electrically conductive material and communicates with an electrical ground, and the injector needle comprises an inside surface and a non-metallic, electrically conductive coating on the inside surface;
at least a portion of the injector needle is composed of or coated with an antistatic plastic and communicates with an electrical ground, wherein liquid flowing through the injector needle is exposed to the antistatic plastic; and
the sample analyzing apparatus comprises a plastic tube fluidly coupled between the pump and the injector needle, the plastic tube is composed of or coated with an antistatic plastic and communicating with an electrical ground, wherein liquid flowing through the injector needle is exposed to the antistatic plastic.

24. The sample analyzing apparatus of claim 1, comprising a tube fluidly coupled between the pump and the injector needle, and a bubble sensor configured for detecting a bubble in the tube.

25. The sample analyzing apparatus of claim 24, wherein the bubble sensor is configured for transmitting an output signal to the pump or a pump controller controlling the pump in response to detecting a bubble.

26. The sample analyzing apparatus of claim 1, wherein the injector assembly comprises a light guide extending through the injector housing and configured for communicating with the luminescence detector.

27. A sample analyzing apparatus, comprising:
an apparatus housing;
a sample carrier disposed in the apparatus housing and configured for supporting a sample;
a reservoir support configured for supporting a reagent reservoir;
a pump configured for communicating with the reagent reservoir;

an injector assembly disposed in the apparatus housing, and comprising:
   an injector housing;
   an injector needle extending through the injector housing and configured for communicating with the reagent reservoir via the pump; and
   a light guide extending through the injector housing;
a driver configured for moving the injector assembly toward and away from the sample carrier; and
a luminescence detector positioned in the apparatus housing to receive optical signals from the sample via the light guide,
wherein the injector housing comprises a distal housing end, the injector needle comprises a needle outlet at the distal housing end, and the injector assembly comprises a liquid sensor configured for detecting liquid at the housing end, the liquid sensor comprising an electrically conductive tube surrounding the light guide and configured for communicating with electronics configured for detecting an electrical current between the electrically conductive tube and the injector needle or between the electrically conductive tube and the injector housing.

28. The sample analyzing apparatus of claim 27, wherein the sample carrier is movable to align the injector assembly with a sample contained on the sample carrier.

29. The sample analyzing apparatus of claim 27, comprising a luminescence cartridge removably mounted at the sample analyzing apparatus, the luminescence cartridge comprising a cartridge housing comprising a cartridge housing opening, wherein the driver, the reservoir support and the pump are disposed in the cartridge housing, and the injector assembly is at least partially disposed in the cartridge housing and is movable by the driver through the cartridge housing opening and alternately toward and away from the sample carrier.

* * * * *